US012582823B2

(12) United States Patent
Isaacson et al.

(10) Patent No.: US 12,582,823 B2
(45) Date of Patent: Mar. 24, 2026

(54) FLEXIBLE STIMULATION PATTERNING FRAMEWORK

(71) Applicant: Medtronic, Inc., Minneapolis, MN (US)

(72) Inventors: Benjamin P. Isaacson, Mahtomedi, MN (US); Brett M. Nelson, Shoreview, MN (US); Duane L. Bourget, Andover, MN (US); Nicholas D. Buse, New Brighton, MN (US); Laura A. Skarie, Deephaven, MN (US); David E. Linde, Bremerton, WA (US)

(73) Assignee: Medtronic, Inc., Minneapolis, MN (US)

( * ) Notice: Subject to any disclaimer, the term of this patent is extended or adjusted under 35 U.S.C. 154(b) by 428 days.

(21) Appl. No.: 18/178,430

(22) Filed: Mar. 3, 2023

(65) Prior Publication Data

US 2023/0321442 A1 Oct. 12, 2023

Related U.S. Application Data

(60) Provisional application No. 63/362,492, filed on Apr. 5, 2022.

(51) Int. Cl.
*A61N 1/00* (2006.01)
*A61N 1/05* (2006.01)
(Continued)

(52) U.S. Cl.
CPC ....... *A61N 1/36132* (2013.01); *A61N 1/0551* (2013.01); *A61N 1/37211* (2013.01)

(58) Field of Classification Search
CPC .............. A61N 1/36132; A61N 1/0551; A61N 1/37211; A61N 1/36062; A61N 1/36139;
(Continued)

(56) References Cited

U.S. PATENT DOCUMENTS 7,228,179 B2 * 6/2007 Campen ............. A61B 17/3468
607/46
10,449,369 B2 10/2019 Goetz
(Continued)

OTHER PUBLICATIONS

International Search Report and Written Opinion of International Application No. PCT/IB2023/052250 dated Jun. 9, 2023, 15 pp.

*Primary Examiner* — Scott M. Getzow
(74) *Attorney, Agent, or Firm* — Shumaker & Sieffert, P.A.

(57) ABSTRACT

A system to provide flexible stimulation pattern definition, delivery, and control to dynamically adjust a therapy regimen for electrical stimulation therapy based on patient needs. Firmware in an electrical stimulation delivery device that executes the therapy regimen may be implemented as a "player" of a series of instructions for the received stimulation patterns. The system may include a wearable device or an implantable device. An external computing device configured to program the electrical stimulation delivery device may include a stimulation pattern construct collection from which a clinician can select, assemble, and modify waveforms, bursts, pattern, sensing or other event triggers etc. to create a therapy regimen. The external computing device may transmit software that defines the selected regimen to the electrical stimulation delivery device memory, where the device "plays" the instructions to deliver electrical stimulation according to the therapy regimen.

23 Claims, 10 Drawing Sheets

(51) Int. Cl.
    *A61N 1/36*         (2006.01)
    *A61N 1/372*       (2006.01)

(58) Field of Classification Search
    CPC .......................... A61N 1/36142–36178; A61N
                                   1/37252–37264
    See application file for complete search history.

(56)                     References Cited

U.S. PATENT DOCUMENTS

| | | |
|---|---|---|
| 10,449,371 B2 | 10/2019 | Serrano Carmona |
| 10,675,468 B2 | 6/2020 | Torgerson |
| 10,737,095 B2 | 8/2020 | Burdick et al. |
| 2007/0027501 A1 | 2/2007 | Jensen et al. |
| 2011/0040546 A1 | 2/2011 | Gerber et al. |
| 2015/0057717 A1 | 2/2015 | Wu et al. |
| 2015/0157864 A1* | 6/2015 | Rosenberg ......... A61N 1/36171 |
| | | 607/62 |
| 2018/0117345 A1 | 5/2018 | Parker |
| 2018/0193653 A1 | 7/2018 | Bokil |
| 2019/0083798 A1 | 3/2019 | Bachinski et al. |
| 2019/0262622 A1 | 8/2019 | Wechter |
| 2019/0329024 A1 | 10/2019 | Kothandaraman et al. |
| 2020/0306542 A1 | 10/2020 | Giftakis et al. |
| 2021/0031032 A1* | 2/2021 | Zirpel ................ A61N 1/36164 |
| 2021/0046322 A1 | 2/2021 | Zhang et al. |

* cited by examiner

322

HOUSING
324

MEMORY
352

PRIMARY
PROCESSING
CIRCUITRY
350

USER
INTERFACE
354

AUDIO OUTPUT
CIRCUITRY
370

357

TELEMETRY
CIRCUITRY
356

CHARGING
CIRCUITRY
368

329

POWER
SOURCE
360

328

NETWORK
COMPUTING
DEVICE
312

TEMPERATURE SENSOR
359

CHARGING
CIRCUITRY
358

348

CHARGING WAND
326

Schedule:          Alarms:
A – indefinite     B @ 6am
B – indefinite     A @ 6pm
C – indefinite Time (24 hrs)

720

12 am

Schedule:          Alarms:
A – indefinite     B @ 6am
B – indefinite     A @ 6pm Time (24 hrs)

12 am

FLEXIBLE STIMULATION PATTERNING FRAMEWORK

This application claims the benefit of U.S. Provisional Patent Application 63/362,492, filed Apr. 5, 2022, the entire content of which is incorporated herein by reference.

TECHNICAL FIELD

The disclosure relates to delivery of electrical stimulation therapy by a medical device.

BACKGROUND

Medical devices may be external or implanted and may be used to deliver electrical stimulation therapy to patients via various tissue sites to treat a variety of symptoms or conditions such as chronic pain, tremor, Parkinson's disease, epilepsy, urinary or fecal incontinence, sexual dysfunction, obesity, or gastroparesis. A medical device may deliver electrical stimulation therapy via one or more leads that include electrodes located proximate to target locations associated with the brain, the spinal cord, pelvic nerves, peripheral nerves, or the gastrointestinal tract of a patient. Stimulation proximate the spinal cord, proximate the sacral nerve, within the brain, and proximate peripheral nerves are often referred to as spinal cord stimulation (SCS), sacral neuromodulation (SNM), deep brain stimulation (DBS), tibial stimulation and peripheral nerve stimulation (PNS).

Electrical stimulation may be delivered to a patient by the medical device in a train of electrical pulses, and parameters of the electrical pulses may include a frequency, an amplitude, a pulse width, and a pulse shape.

SUMMARY

In general, the disclosure describes a system to provide flexible stimulation pattern definition, delivery, and control to dynamically adjust a therapy regimen for electrical stimulation therapy based on patient needs. Firmware that executes the therapy regimen may be implemented as a "player" of a series of instructions for received stimulation patterns. That is, this disclosure describes example techniques of utilizing software that is stored on a medical device, and is called by firmware (e.g., which may be but is not limited to being an operating system) of the medical device to execute and cause the medical device to deliver therapy in accordance with the software. The system may include a wearable device, such as for acute therapy delivery or an implantable device used for chronic therapy delivery.

Utilizing software to program the medical device to deliver therapy may provide for a flexible, extensible manner in which to program the medical device to deliver therapy. For instance, some techniques that utilize programmable ways in which to deliver therapy are limited in the therapy that the medical device can deliver. As an example, a user may input therapy parameters into predefined stimulation patterns construct provided by firmware executing on the medical device. Therapy parameters may include selecting timing, pulse magnitude, pulse width, burst pattern and so on. The medical device may deliver therapy in accordance the predefined stimulation patterns and the therapy parameters. However, in one or more examples described in this disclosure, rather than inputting just therapy parameters, a user may load software (e.g., source code to be compiled by the medical device, or object code that has been compiled by the programmer) on to the medical device, where the software defines the stimulation pattern construct, including patterns, magnitude, timing and other parameters for the medical device to deliver. Rather than being limited to predefined stimulation patterns defined in the firmware, the firmware in the device of this disclosure may call the software to be executed on the medical device, which allows the medical device to deliver therapy in accordance with the stimulation pattern construct defined by the software that is not restricted to a predefined stimulation pattern in the firmware, as found in other examples of medical devices.

An external computing device configured to program the therapy delivery device may include a stimulation pattern construct collection from which a clinician can select, assemble, and modify waveforms, bursts, patterns etc. to create a tailored therapy regimen directed to treat symptoms for a particular patient, can further be tailored as needed for that patient. Some examples applications of the system of this disclosure may include to: address a variety of conditions/diseases, update the therapy regimen as the patient's disease evolves, or the patient's body becomes less responsive an applied regimen, i.e., to adjust for plasticity associated with effective therapy, to make adjustments to improve efficacy of the therapy and so on. The external computing device, also called a programmer in this disclosure, may output the selected regimen or suite of regimens into software based on the user input. As noted above, in some examples, the external computing device may compile the selected regimen(s) into software comprising machine instructions (opcodes), which may also be referred to as object code in this disclosure. In other examples, the external computing device may arrange the selected therapy regimen(s) into software comprising source code to be compiled by the medical device. The external computing device may transmit, e.g., download, the software to the therapy delivery device memory. The processing circuitry of the device executes firmware configured to "play" the downloaded software, e.g., control therapy delivery circuitry of the medical device to output the therapy regimen.

In one example, this disclosure describes a medical system comprising a user interface with a display and input device; first processing circuitry operably coupled to the user interface, the first processing circuitry configured to: cause the user interface to present a stimulation pattern construct collection to a user; receive user input to define a stimulation pattern responsive to presenting the stimulation pattern construct collection to the user; generate software comprising one of object code or source code based on the defined stimulation pattern; transmit the software; and an implantable medical device comprising: stimulation circuitry configured to deliver electrical stimulation to a patient via a plurality of electrodes implanted proximal to tissue of the patient; a memory configured to store the software received from the external computing device; and second processing circuitry operably coupled to the memory, the second processing circuitry configured to execute firmware that: causes the second processing circuitry to access the received software; and control the stimulation circuitry based on the execution of the received software to deliver the defined stimulation pattern.

In another example, this disclosure describes a method comprising controlling, by processing circuitry of an external computing device, a user interface operably coupled to the processing circuitry, to present a stimulation pattern construct collection to a user, wherein the stimulation pattern construct collection defines a plurality of elements for electrical stimulation; responsive to presenting the stimulation pattern construct collection to the user, receiving by the processing circuitry and via the user interface, user input to define a stimulation pattern; generating, by the processing circuitry, software comprising one of object code or source code based on the defined stimulation pattern; transmitting, by the processing circuitry, the software; receiving, by an implantable medical device, the software from the external computing device; storing, by the implantable medical device, the software at a memory of the implantable medical device; executing, by the implantable medical device, firmware that: accesses the received software; and controls stimulation circuitry of the implantable medical device, based on the execution by the firmware of the received software; delivering, by the implantable medical device, the defined stimulation pattern based on the stored software.

In another example, this disclosure describes a medical device comprising stimulation circuitry configured to deliver electrical stimulation to a patient via a plurality of electrodes implanted proximal to tissue of the patient; a memory configured to store software received from an external computing device the software comprising one of object code or source code based on a defined stimulation pattern to be delivered to the patient; and processing circuitry operably coupled to the memory, the processing circuitry configured to configured to execute firmware that: causes the processing circuitry to access the received software; and control the stimulation circuitry based on the execution of the received software to deliver the defined stimulation pattern.

The details of one or more examples of the disclosure are set forth in the accompanying drawings and the description below. Other features, objects, and advantages of the disclosure will be apparent from the description and drawings, and from the claims.

DETAILED DESCRIPTION

Figure 1:
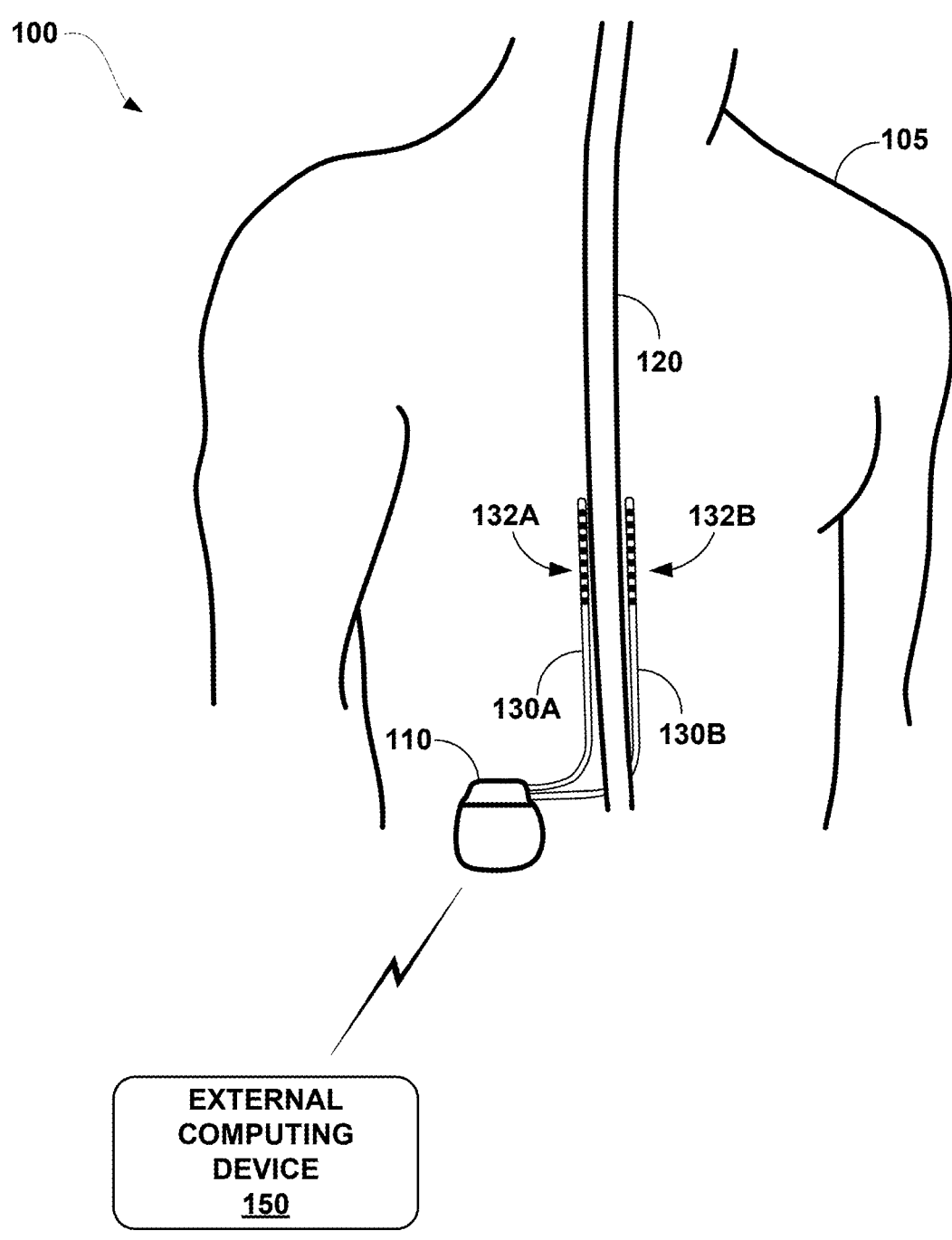
FIG. 1 is a conceptual diagram illustrating an example system that includes an implantable medical device (IMD) configured to deliver spinal cord stimulation (SCS) therapy and an external programmer, in accordance with one or more techniques of this disclosure.

The disclosure describes a system to provide flexible stimulation pattern definition, delivery, and control to dynamically adjust a therapy regimen for electrical stimulation therapy based on patient needs. As described in more detail, firmware may call on software that defines the therapy regimen so that the firmware may be implemented as a "player" to interpret a series of instructions defined by the software for received stimulation patterns. The system may include a wearable device, such as for acute therapy delivery or an implantable device used for chronic therapy delivery.

In contrast to some examples of therapy delivery devices, which typically include firmware with defined logic, and therapy waveforms that are only customizable by a selection of parameters (amplitude, pulse width, on-time, off-time, etc.), the medical device described in this disclosure may include a processor, stimulation and sensing circuitry, but only limited firmware that executes software saved in memory to output a defined therapy regimen defined by the software, rather than therapy waveforms pre-defined by the firmware. The therapy regimen in the received software may include interrupts, such as a specific time or event, that may trigger the medical device to cease outputting a first therapy program of the therapy regimen and start a second therapy program.

An external computing device configured to program the therapy delivery device of this disclosure may store and display a stimulation pattern construct collection from which a clinician can select, assemble, and modify waveforms, bursts, patterns etc. to create a therapy regimen that can be modified as needed. Some examples applications may include: to address a variety of conditions/diseases, update the therapy regimen as the patient's disease evolves, or the patient's body becomes less responsive to an applied regimen, i.e., to adjust for plasticity associated with effective therapy, to make adjustments to improve efficacy of the therapy and so on. The external computing device, also called a programmer in this disclosure, in some examples may compile the user selected therapy program, or regimen of a suite of therapy programs into software comprising machine instructions (opcodes) and may download the software to the therapy delivery device memory, where the device "plays" the opcode to output the therapy regimen. In other examples, the external computing device may convert the user selected therapy program, or regimen of a suite of therapy programs into software comprising source code, download to the medical device and the medical device may perform the compile step to deliver the therapy regimen.

The system, including the programmer and therapy delivery device, may allow flexible stimulation pattern definition, delivery, and control to dynamically adjust a therapy regimen based on patient needs. Firmware that executes the therapy regimen may be implemented to interpret the received and stored instructions, e.g., as a "player" of the instructions for the received defined stimulation pattern.

In this manner, the system of this disclosure is configured to deliver complex and unique stimulation pattern e.g., for neuromodulation applications or other medical applications. An advantage of the system of this disclosure is that rather than verifying and validating a device with hardware and firmware configured to perform complex logic that manages a rigid set of therapy programs, the system of this disclosure may include less complex firmware, configured to run the software that have been loaded into device memory. The processing circuitry executing the firmware may manage timers, telemetry, and so on to deliver the defined stimulation patterns in the therapy regimen defined by the downloaded software.

The programmer may include a software "burner," which may allow a human clinician to describe one or many stimulation patterns via assembly of various displayed "building blocks" of waveforms, bursts, etc. The user, e.g., clinician, or other caregiver, may select from validated and verified collection of constructs, e.g., stimulation description language, which may act as the "building blocks" allow the user to be agnostic as to the details of the internals of the therapy delivery device. The system of this disclosure may also include a verified and validated software compiler, configured to take the selected a human readable and human understandable stimulation pattern(s), and decomposes the user selected stimulation patterns into opcode instructions interpretable by the firmware of the therapy delivery device. As noted above, the compiler function may be located either in the programmer or the medical device.

In contrast to the system of this disclosure, therapy delivery devices that include complex firmware to control therapy delivery may need to validate and verify the entire device to be able to deliver any validated new therapy patterns. The verification and validation may test the new firmware that includes any new therapy patterns, but may also need to test all the other functions of the therapy delivery device. The extensive testing, reporting to regulatory bodies, waiting for regulatory analysis and approval may be costly, labor intensive and time consuming.

However, the system of this disclosure may simply need to verify and validate a new therapy pattern for safety and efficacy. In other words, once the programmer function and the therapy delivery device functions have been verified, validated and approved, there may be no need to conduct a full verification of the system to implement a new therapy pattern. Instead, just the new therapy pattern may be tested, validated and submitted for approval, before implementing the new therapy pattern. For example, a new therapy paradigm may adapt to newly discovered neural codes. New research proven to safely stimulate the nervous system could result in a new therapy concept for a given patient population, subpopulation, or phenotype. Such a new pattern, or patterns, once approved, may be delivered to benefit the patient population in weeks rather than months or years that may be needed for a completely new firmware or device rollout.

As noted above, any new electrical stimulation patterns that may provide improved patient outcomes would need to be verified, validated and approved by one or more oversight processes, such as the Food and Drug Administration approval in the U.S., a conformity assessment in Europe, and so on. As noted above, the techniques of this disclosure may allow effective new stimulation patterns to be deployed for patient use without the delays, cost and expense involved in a complete validation of an entire system. Moreover, the example techniques may not be limited to types of stimulation patterns that can be delivered. For instance, some medical devices may include constructs that allow defining pulse width, amplitude, frequency, time duration information as well as to respond to sensed signals, e.g., physiological signals such as patient movement, posture, blood chemistry, bioelectrical signals and so on. However, there was no control to interrupt therapy, generate overlapping therapies, etc. By defining therapy in form of software that is accessed and executed, the example techniques provide for ways for flexible, extensible stimulation pattern definitions.

In addition, the system of this disclosure may be employed to allow studying of stimulation patterns to determine which scientific ideas have the most promise to try and deliver to the patient population. Once approved, the new therapy pattern may be included in the list of constructs in the programmer, which may be selected and loaded to a patient's device. In this manner, the system of this disclosure may allow therapy delivery devices to be more tolerant of stimulation pattern idea changes and adapt to be able to deliver the new therapy patterns, which may improve patient outcomes, without the delays and expense of new firmware, software implementation or device testing.

FIG. 1 is a conceptual diagram illustrating an example system 100 that includes an IMD 110 configured to deliver spinal cord stimulation (SCS) therapy and an external computing device 150, in accordance with one or more techniques of this disclosure. Although the techniques described in this disclosure are generally applicable to a variety of medical devices including external devices and IMDs, application of such techniques to IMDs and, more particularly, implantable electrical stimulators (e.g., neurostimulators) will be described for purposes of illustration. More particularly, the disclosure will refer to an implantable SCS system for purposes of illustration, but without limitation as to other types of medical devices or other therapeutic applications of medical devices. In other words, the techniques of this disclosure may also apply to other devices, including wearable devices, that may be located elsewhere on patient 105. In other examples, IMD 110 may take the form of any combination of deep brain stimulation (DBS) devices, pelvic health devices, tibial stimulation device, implantable cardioverter defibrillators (ICDs), pacemakers, cardiac resynchronization therapy devices (CRT-Ds), left ventricular assist devices (LVADs) and so on.

As shown in FIG. 1, system 100 includes an IMD 110, leads 130A and 130B, and external computing device 150 shown in conjunction with a patient 105, who is ordinarily a human patient. In the example of FIG. 1, IMD 110 is an implantable electrical stimulator that is configured to generate and deliver electrical stimulation therapy to patient 105 via one or more electrodes of electrodes of leads 130A and/or 130B (collectively, "leads 130"), e.g., for relief of chronic pain or other symptoms. For the example of FIG. 1, IMD 110 may also be referred to as implantable neurostimulator (INS).

In some examples, IMD 110 may be coupled to a single lead carrying multiple electrodes or more than two leads each carrying multiple electrodes. IMD 110 may include an electrical connector configured to connect to the electrical leads, e.g., in the header of IMD 110. In some examples, the stimulation signals, or pulses, may be configured to elicit detectable ECAP signals that IMD 110 may use, along with other sensors to determine the posture state occupied by patient 105 and/or determine how to adjust one or more parameters that define stimulation therapy. IMD 110 may be a chronic electrical stimulator that remains implanted within patient 105 for weeks, months, or even years. In other examples, IMD 110 may be a temporary, or trial, stimulator used to screen or evaluate the efficacy of electrical stimulation for chronic therapy. In one example, IMD 110 is implanted within patient 105, while in another example, IMD 110 is an external device coupled to percutaneously implanted leads. In some examples, IMD 110 uses one or more leads, while in other examples, IMD 110 is leadless.

IMD 110 may be configured to receive one or more stimulation patterns from external computing device 150. Processing circuitry of IMD 110 may cause stimulation circuitry of IMD 110 to output electrical stimulation therapy according to the one or more stimulation patterns. Some examples of stimulation patterns may include any combination of stimulation parameters such as the number of pulses in a burst, the number of bursts over a duration, the pulse width of a pulse in a burst, the ON-time, the OFF-time, a pattern of pulses over a duration and other parameters.

A caregiver may select and/or define the one or more stimulation patterns based on the needs of patient 105 to adjust the efficacy of the therapy to relieve the patient's symptoms. The one or more defined stimulation patterns may define a therapy regimen. In other words, a therapy regimen may include a first stimulation pattern delivered at a first time for a first duration, a second stimulation pattern delivered at a second time for a second duration, and so on. In some examples, the selected stimulation pattern, and the duration, may be delivered in a pre-defined order. In other examples, the selected stimulation pattern, or patterns, may be invoked based on certain events or conditions. For example, the processing circuitry of IMD 110 may have received a therapy regimen from external computing device 150 that includes a defined stimulation pattern to be delivered based on a time of day, a sensed activity of patient 105, such as a sleep state or awake state, a sensed change in body chemistry, a sensed bioelectrical signal, in response to patient input, or some other event or condition. In the absence of the event, or condition, processing circuitry of IMD 110 may deliver a stimulation pattern, or patterns according to the received therapy regimen.

IMD 110 may be constructed of any polymer, metal, or composite material sufficient to house the components of IMD 110 (e.g., components illustrated in FIG. 2) within patient 105. In this example, IMD 110 may be constructed with a biocompatible housing, such as titanium or stainless steel, or a polymeric material such as silicone, polyurethane, or a liquid crystal polymer, and surgically implanted at a site in patient 105 near the pelvis, abdomen, or buttocks. In other examples, IMD 110 may be implanted within other suitable sites within patient 105, which may depend, for example, on the target site within patient 105 for the delivery of electrical stimulation therapy. The outer housing of IMD 110 may be configured to provide a hermetic seal for components, such as a rechargeable or non-rechargeable power source. In addition, in some examples, the outer housing of IMD 110 is selected from a material that facilitates receiving energy to charge the rechargeable power source.

Electrical stimulation energy, which may be constant current or constant voltage-based pulses, for example, is delivered from IMD 110 to one or more target tissue sites of patient 105 via one or more electrodes (not shown) of implantable leads 130. In the example of FIG. 1, leads 130 carry electrodes that are placed adjacent to the target tissue of spinal cord 120. One or more of the electrodes may be disposed at a distal tip of a lead 130 and/or at other positions at intermediate points along the lead. Leads 130 may be implanted and coupled to IMD 110. The electrodes may transfer electrical stimulation generated by an electrical stimulation generator in IMD 110 to tissue of patient 105. Although leads 130 may each be a single lead, lead 130 may include a lead extension or other segments that may aid in implantation or positioning of lead 130. In some other examples, IMD 110 may be a leadless stimulator with one or more arrays of electrodes arranged on a housing of the stimulator rather than leads that extend from the housing. In addition, in some other examples, system 100 may include one lead or more than two leads, each coupled to IMD 110 and directed to similar or different target tissue sites.

The electrodes 132A and 132B of leads 130 may be electrode pads on a paddle lead, circular (e.g., ring) electrodes surrounding the body of the lead, conformable electrodes, cuff electrodes, segmented electrodes (e.g., electrodes disposed at different circumferential positions around the lead instead of a continuous ring electrode), any combination thereof (e.g., ring electrodes and segmented electrodes) or any other type of electrodes capable of forming unipolar, bipolar or multipolar electrode combinations for therapy. Ring electrodes arranged at different axial positions at the distal ends of lead 130 will be described for purposes of illustration.

The deployment of electrodes 132A and 132B via leads 130 is described for purposes of illustration, but arrays of electrodes may be deployed in different ways. For example, a housing associated with a leadless stimulator may carry arrays of electrodes, e.g., rows and/or columns (or other patterns), to which shifting operations may be applied. Such electrodes may be arranged as surface electrodes, ring electrodes, or protrusions. As a further alternative, electrode arrays may be formed by rows and/or columns of electrodes on one or more paddle leads. In some examples, electrode arrays include electrode segments, which are arranged at respective positions around a periphery of a lead, e.g., arranged in the form of one or more segmented rings around a circumference of a cylindrical lead. In other examples, one or more of leads 130 are linear leads having 8 ring electrodes along the axial length of the lead. In another example, the electrodes are segmented rings arranged in a linear fashion along the axial length of the lead and at the periphery of the lead.

The therapy regimen received from external computing device 150, may include stimulation patterns that define stimulation parameters for each pattern. Some examples of stimulation parameters for a defined stimulation pattern may include information identifying which electrodes have been selected for delivery of stimulation according to the stimulation pattern, the polarities of the selected electrodes, i.e., the electrode combination for the defined pattern, voltage or current amplitude, pulse frequency, pulse width, pulse shape of stimulation delivered by electrodes 132. In some examples, parameters may include sequences of pulses, for example a "burst" of pulses with gradually increasing current magnitudes, or some other sequence. In some examples, a stimulation pattern may cause IMD 110 to deliver therapy for a given duration and stop delivering therapy for a given duration. In other words, parameters of the electrical stimulation therapy may include an ON-time and an OFF-time. In some examples, an ON-time may be a few seconds or minutes and the OFF-time may also be for a few seconds or minutes. The ON-time may be equal to the OFF-time in some examples, while in other examples the ON-time and the OFF-time may be different durations.

These stimulation patterns and the associated parameters values that make up the stimulation pattern may be selected by a user, e.g., a health care provider, using external computing device 150. A user interface for external computing device 150 may provide flexible stimulation pattern definition, delivery, and control to dynamically adjust a therapy regimen for electrical stimulation therapy based the needs of patient 105. IMD 110 may receive and store software defining the therapy regimen. Firmware executed by processing circuitry of IMD 110 may be implemented as a "player" of the instructions to interpret the received software, e.g., in the form of opcodes, and deliver stimulation patterns defined by the software via electrical stimulation circuitry coupled to electrodes 132.

Although FIG. 1 is directed to SCS therapy, e.g., used to treat pain, in other examples system 100 may be configured to treat any other condition that may benefit from electrical stimulation therapy. For example, system 100 may be used to treat tremor, Parkinson's disease, epilepsy, a pelvic floor disorder (e.g., urinary incontinence or other bladder dysfunction, fecal incontinence, pelvic pain, bowel dysfunction, or sexual dysfunction), obesity, gastroparesis, or psychiatric disorders (e.g., depression, mania, obsessive compulsive disorder, anxiety disorders, and the like). In this manner, system 100 may be configured to provide therapy taking the form of deep brain stimulation (DBS), peripheral nerve stimulation (PNS), peripheral nerve field stimulation (PNFS), cortical stimulation (CS), pelvic floor stimulation, gastrointestinal stimulation, cardiac or any other stimulation therapy capable of treating a condition of patient 105.

In some examples, lead 130 includes one or more sensors configured to allow IMD 110 to monitor one or more parameters of patient 105, such as patient activity, pressure, temperature, or other characteristics. The one or more sensors may be provided in addition to, or in place of, therapy delivery by lead 130.

IMD 110 is configured to deliver electrical stimulation therapy to patient 105 via selected combinations of electrodes carried by one or both of leads 130, alone or in combination with an electrode carried by or defined by an outer housing of IMD 110. The target tissue for the electrical stimulation therapy may be any tissue affected by electrical stimulation, which may be in the form of electrical stimulation pulses or continuous waveforms. In some examples, the target tissue includes nerves, smooth muscle or skeletal muscle. In the example illustrated by FIG. 1, the target tissue is tissue proximate spinal cord 120, such as within an intrathecal space or epidural space of spinal cord 120, or, in some examples, adjacent nerves that branch off spinal cord 120. Leads 130 may be introduced into spinal cord 120 in via any suitable region, such as the thoracic, cervical or lumbar regions. Stimulation of spinal cord 120 may, for example, prevent pain signals from traveling through spinal cord 120 and to the brain of patient 105. Patient 105 may perceive the interruption of pain signals as a reduction in pain and, therefore, efficacious therapy results. In other examples, stimulation of spinal cord 120 may produce paresthesia which may be reduce the perception of pain by patient 105, and thus, provide efficacious therapy results.

As described herein, information may be transmitted between external computing device 150 and IMD 110. Therefore, IMD 110 and external computing device 150 may communicate via wireless communication using any techniques known in the art. Examples of communication techniques may include, for example, radiofrequency (RF) telemetry and inductive coupling, but other techniques are also contemplated. In some examples, external computing device 150 includes a communication head that may be placed proximate to the patient's body near the IMD 110 implant site to improve the quality or security of communication between IMD 110 and external computing device 150. Communication between external computing device 150 and IMD 110 may occur during power transmission or separate from power transmission.

In some examples, IMD 110, in response to commands from external computing device 150, delivers electrical stimulation therapy to a target tissue site of the spinal cord 120 of patient 105 via electrodes 132 on leads 130 according to a therapy regimen consisting of one or more therapy stimulation patterns. In some examples, IMD 110 may insert or change a therapy pattern based on an event, or condition. A therapy regimen may change as therapy needs of patient 105 evolve over time. When patient 105 receives the same therapy for an extended period, the efficacy of the therapy may be reduced.

In some examples, IMD 110 may include the stimulation circuitry, the sensing circuitry, and the processing circuitry. However, in other examples, one or more additional devices may be part of the system that performs the functions described herein. For example, IMD 110 may include the stimulation circuitry and the sensing circuitry, but external computing device 150 or other external device may include the processing circuitry that process received data and perform calculations. Therefore, the processes described herein may be performed by multiple devices in a distributed system. In some examples, system 100 may include one or more electrodes that deliver and/or sense electrical signals. Such electrodes may be configured to sense the ECAP signals. In some examples, the same electrodes may be configured to sense signals representative of transient movements of the patient. In other examples, other sensors, such as accelerometers, gyroscopes, or other movement sensors may be configured to sense movement of the patient that indicates the patient may have transitioned to a different posture state, by which the target characteristic value may have changed accordingly.

Figure 2:
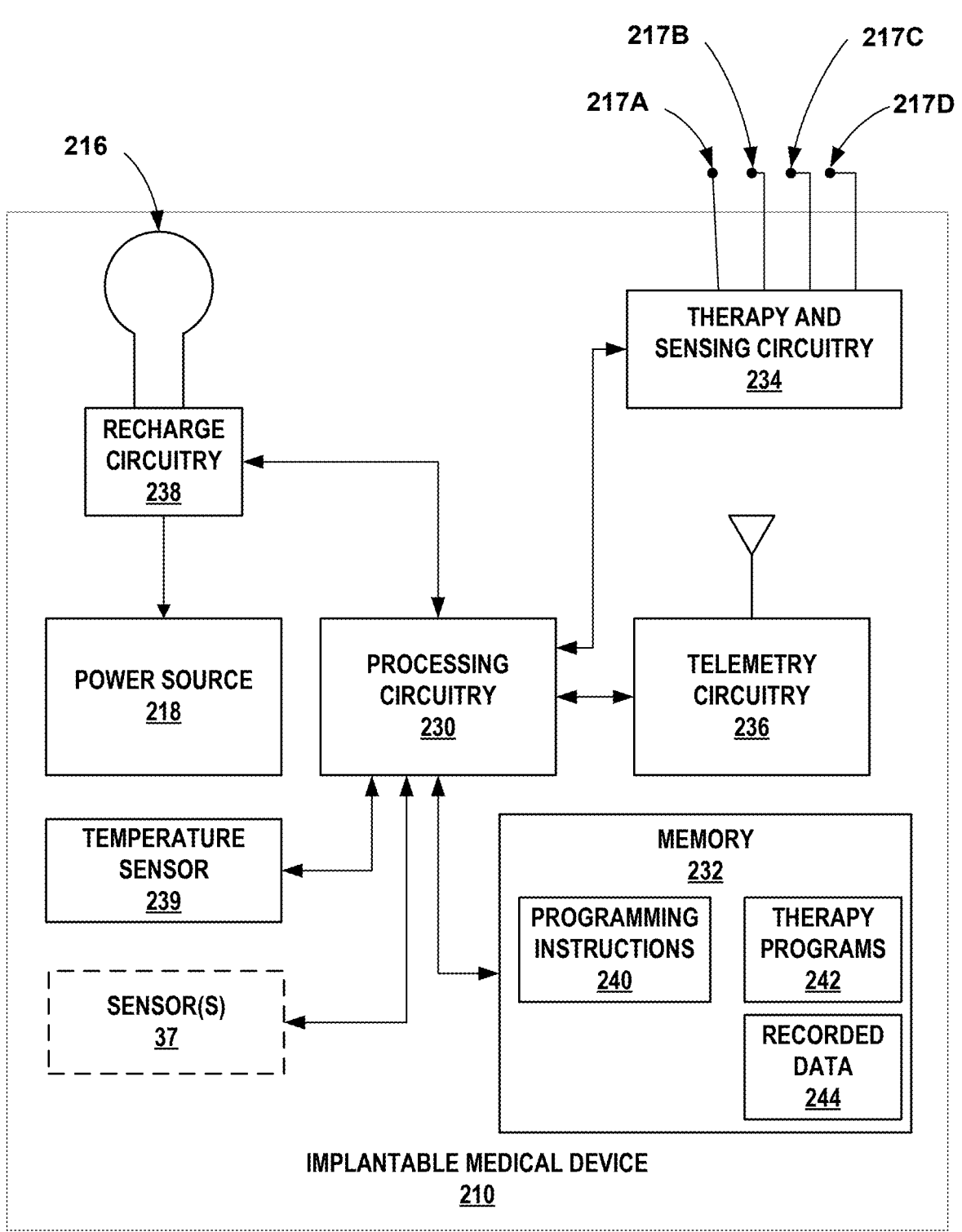
FIG. 2 is a block diagram illustrating example components of the implantable medical device of FIG. 1.

FIG. 2 is a block diagram illustrating example components of the medical device of FIG. 1. Implantable medical device 210 is an example of IMD 110 described above in relation to FIG. 1. In the example illustrated in FIG. 2, IMD 210 includes temperature sensor 239, coil 216, processing circuitry 230, therapy and sensing circuitry 234, recharge circuitry 238, memory 232, telemetry circuitry 236, power source 218, and one or more sensors 237, such as an accelerometer. In other examples, IMD 210 may include a greater or a fewer number of components, e.g., in some examples, IMD 210 may not include temperature sensor 239 or sensors 237. In general, IMD 210 may comprise any suitable arrangement of hardware, alone or in combination with software and/or firmware, to perform the various techniques described herein attributed to IMD 210 and processing circuitry 230, and any equivalents thereof.

Processing circuitry 230 of IMD 210 may include one or more processors, such as one or more microprocessors, digital signal processors (DSPs), application specific integrated circuits (ASICs), field programmable gate arrays (FPGAs), or any other equivalent integrated or discrete logic circuitry, as well as any combinations of such components. IMD 210 may include a memory 232, such as random access memory (RAM), read only memory (ROM), programmable read only memory (PROM), erasable programmable read only memory (EPROM), electronically erasable programmable read only memory (EEPROM), flash memory, comprising executable instructions for causing the processing circuitry 230 to perform the actions attributed to this circuitry. Moreover, although processing circuitry 230, therapy and sensing circuitry 234, recharge circuitry 238, telemetry circuitry 236, and temperature sensor 239 are described as separate modules, in some examples, some combination of processing circuitry 230, therapy and sensing circuitry 234, recharge circuitry 238, telemetry circuitry 236 and temperature sensor 239 are functionally integrated. In some examples, processing circuitry 230, therapy and sensing circuitry 234, recharge circuitry 238, telemetry circuitry 236, and temperature sensor 239 correspond to individual hardware units, such as ASICs, DSPs, FPGAs, or other hardware units. In this disclosure, therapy, and sensing circuitry 234 may be referred to as therapy circuitry 234, for simplicity.

Memory 232 may store software that specify therapy patterns and therapy regimens, that when executed by processing circuitry 230, cause electrical stimulation circuitry therapy circuitry 234 to deliver electrical stimulation therapy to a target tissue, e.g., a target nerve of a patient. As described above in relation to FIG. 1, processing circuitry 230 may receive software from external device 150, depicted in FIG. 1, that include one or more therapy regimens that include one or more therapy patterns.

In contrast to other implementations of an electrical stimulation medical device, programming instructions 240 may include only a limited set of instructions directed to electrical stimulation delivery. Programming instructions 240 may be considered firmware and include instructions for recharging rechargeable power source 218, instructions for communication between IMD 210 and an external computing device, or other instructions required to perform tasks attributed to IMD 210.

Unlike other implementations, therapy programs 242 may store received software from an external computing device, e.g., external computing device 150 described above in relation to FIG. 1. The software may include a defined stimulation pattern, or a therapy regimen that includes a plurality of defined stimulation patterns, that are based on stimulation patterns selected from a stimulation pattern construct collection presented to a user, e.g., a health care provider, by the external computing device. Processing circuitry 230 may execute the limited programming instructions (firmware) in programming instructions 240 to interpret the software received from the external computing device to determine the defined stimulation pattern. Processing circuitry 230 may control the stimulation circuitry, e.g., therapy circuitry 234, to deliver the defined stimulation pattern to the patient based only on the stored software in therapy programs 242 received from the external computing device. In some examples the software may include a therapy regimen with several stimulation patterns, e.g., a first defined stimulation pattern and a second defined stimulation pattern. The various stimulation patterns may be different from each other defined stimulation pattern, e.g., defined to elicit a specific response from the patient's tissue. Processing circuitry 230 may include timing circuitry, and based on the stored instructions in therapy programs 242, processing circuitry 230 may control therapy circuitry 234 according to the first defined stimulation pattern for a first duration, and control therapy circuitry 234 according to the second defined stimulation pattern for a second duration.

In some examples, the therapy regimen comprises a third, fourth, fifth and so on defined stimulation patterns. Processing circuitry 230 may be configured, in some examples, to receive an indication, during the first duration or the second duration, to control the stimulation circuitry to deliver the third defined stimulation pattern, or some other pattern. In response to receiving the indication, processing circuitry 230 may control therapy circuitry 234 to deliver the third defined stimulation pattern for some third duration.

In contrast to the configuration of memory 232, some other implementations of a memory for an IMD may instead include detailed instructions in the firmware with programming instructions describing each of the available stimulation patterns. An IMD with such a configuration may receive instructions from a programmer, but the instructions may only include a few selectable parameters for the available stimulation patterns pre-defined in the firmware, such as a pulse magnitude, a pulse width, burst length, and so on. The processing circuitry may store these parameters at the memory and configure the stimulation circuitry of such an IMD to output stimulation pattern as modified by the received parameters. A health care provider may make adjustments to available parameters for the available therapy patterns available in the firmware located at the memory of the IMD.

These instructions containing selected parameters differ from the software of this disclosure that include one or more defined stimulation patterns, along with associated parameters, stored at therapy programs 242, as described above. In the example of IMD 210, a health care provider may change an entire therapy regimen stored at therapy programs 242 of memory 232, rather than just being limited to adjusting a few parameters, as in other examples of IMDs.

Memory 232 may also store data, at recorded data 244, such as sensed events, measured local field potentials, and so on. In some examples, memory 232 may also store temperature data from temperature sensor 239 at recorded data 244.

Therapy and sensing circuitry 234 may generate and deliver electrical stimulation under the control of processing circuitry 230. In some examples, processing circuitry 230 controls therapy circuitry 234 by accessing memory 232 to selectively access and execute at least one of the stimulation patterns from therapy programs 242. As described above in relation to FIG. 1, the instructions containing the stimulation patterns from the external computing device may include parameters such as voltage amplitude, a current amplitude, a pulse rate, a pulse width, a duty cycle, along with which combination of electrodes 217A, 217B, 217C, and 217D (collectively "electrodes 217") that therapy circuitry 234 may use to deliver the electrical stimulation signal. Stimulation patterns may also include changes in parameters, such as a ramp up or ramp down in magnitude, specified patterns of different pulse widths and so on.

In other examples, IMD 210 may have more or fewer electrodes than the four shown in the example of FIG. 2. In some examples electrodes 217 may be part of or attached to a housing of IMD 210, e.g., a leadless electrode. In other examples, one or more of electrodes 217 may be part of a lead implanted in or attached to a patient to sense biological signals and/or deliver electrical stimulation, as described above in relation to FIG. 1. In some examples, one or more electrodes connected to therapy circuitry 234 may connect to one or more sensing electrodes, e.g., attached to a housing of IMD 210.

In some examples, IMD 210 may also include components to receive power to recharge rechargeable power source 218 when rechargeable power source 218 has been at least partially depleted. As shown in the example of FIG. 2, IMD 210 includes coil 216 and recharge circuitry 238 coupled to rechargeable power source 218. Recharge circuitry 238 may be configured to charge rechargeable power source 218 with the selected power level determined by either processing circuitry 230 or an external charging device, such as external computing device 150 described above in relation to FIG. 1. Recharge circuitry 238 may include any of a variety of charging and/or control circuitry configured to process or convert current induced in coil 216 into charging current to charge power source 218. Programming instructions for managing recharge circuitry 238 may be stored at the firmware in programming instructions 240.

Secondary coil 216 may include a coil of wire or other device capable of inductive coupling with a primary coil disposed external to patient 12. Although secondary coil 216 is illustrated as a simple loop of in FIG. 2, secondary coil 216 may include multiple turns of conductive wire. Secondary coil 216 may include a winding of wire configured such that an electrical current can be induced within secondary coil 216 from a magnetic field, which may also be called recharge coil 216 in this disclosure. The induced electrical current may then be used to recharge rechargeable power source 218.

Recharge circuitry 238 may include one or more circuits that process, filter, convert and/or transform the electrical signal induced in the secondary coil to an electrical signal capable of recharging rechargeable power source 218. For example, in alternating current induction, recharge circuitry 238 may include a half-wave rectifier circuit and/or a full-wave rectifier circuit configured to convert alternating current from the induction to a direct current for rechargeable power source 218. The full-wave rectifier circuit may be more efficient at converting the induced energy for rechargeable power source 218. However, a half-wave rectifier circuit may be used to store energy in rechargeable power source 218 at a slower rate. In some examples, recharge circuitry 238 may include both a full-wave rectifier circuit and a half-wave rectifier circuit such that recharge circuitry 238 may switch between each circuit to control the charging rate of rechargeable power source 218 and temperature of IMD 210. In some examples recharge circuitry 238 may also include communication circuitry.

Rechargeable power source 218 may include one or more capacitors, batteries, and/or other energy storage devices. Rechargeable power source 218 may deliver operating power to the components of IMD 210. In some examples, rechargeable power source 218 may include a power generation circuit to produce the operating power. Rechargeable power source 218 may be configured to operate through many discharge and recharge cycles. Rechargeable power source 218 may also be configured to provide operational power to IMD 210 during the recharge process. In some examples, rechargeable power source 218 may be constructed with materials to reduce the amount of heat generated during charging. In other examples, IMD 210 may be constructed of materials and/or using structures that may help dissipate generated heat at rechargeable power source 218, recharge circuitry 238, and/or secondary coil 216 over a larger surface area of the housing of IMD 210.

Although rechargeable power source 218, recharge circuitry 238, and secondary coil 216 are shown as contained within the housing of IMD 210, in alternative implementations, at least one of these components may be disposed outside of the housing. For example, in some implementations, secondary coil 216 may be disposed outside of the housing of IMD 210 to facilitate better coupling between secondary coil 216 and the primary coil of the external charging device. In other examples, power source 218 may be a primary power cell and IMD 210 may not include recharge circuitry 238 and secondary coil 216.

Processing circuitry 230 may also control the exchange of information with an external computing device using telemetry circuitry 236. Telemetry circuitry 236 may be configured for wireless communication using radio frequency protocols, such as BLUETOOTH, or similar RF protocols, as well as using inductive communication protocols. Telemetry circuitry 236 may include one or more antennas configured to communicate with an external charging device, for example. Processing circuitry 230 may transmit operational information and receive therapy programs or therapy parameter adjustments via telemetry circuitry 236. In addition, telemetry circuitry 236 may be configured to control the exchange of information related to sensed and/or determined temperature data, for example temperatures sensed by and/or determined from temperatures sensed using temperature sensor 239. In some examples, telemetry circuitry 236 may communicate using inductive communication, and in other examples, telemetry circuitry 236 may communicate using RF frequencies separate from the frequencies used for inductive charging. Programming instructions for communications may be stored as firmware in programming instructions 240.

In some examples, processing circuitry 230 may transmit additional information to an external computing device related to the operation of rechargeable power source 218. For example, processing circuitry 230 may use telemetry circuitry 236 to transmit indications that rechargeable power source 218 is completely charged, rechargeable power source 218 is fully discharged, the amount of charging current output by recharge circuitry 238 e.g., to power source 218, or any other charge status of rechargeable power source 218. In some examples, processing circuitry 230 may use telemetry circuitry 236 to transmit instructions to an external charging device, including instructions regarding further control of the charging session, for example instructions to lower the power level or to terminate the charging session, based on the determined temperature of the housing/external surface of the IMD.

Figure 3:
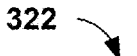
FIG. 3 is a block diagram of an example external computing device of FIG. 1.

FIG. 3 is a block diagram of an example an external computing device of FIG. 1. External computing device 322 in of FIG. 2 is an example of external computing device 150 described above in relation to FIG. 1. In some examples, external computing device 322 may be described as a hand-held device, in other examples, external computing device 322 may be a larger or a non-portable device. In addition, in other examples external computing device 322 may be included as part of an external programmer or include functionality of an external programmer. External computing device 322 may also be referred to as recharger 322, external charging device 322 or programmer 322 in this disclosure.

As shown in the example of FIG. 3, external computing device 322 includes two separate components. Housing 324 encloses components such as a processing circuitry 350, memory 352, user interface 354, telemetry circuitry 356, audio output circuitry 370 and power source 360. Charging head 326, also called charging wand 326, may include charging circuitry 358, temperature sensor 359, and coil 348. Housing 324 is electrically coupled to charging head 326 via charging cable 328. Housing 324 may also include charging circuitry 368 and coil 329, which is an example of coil 329 described above in relation to FIG. 1.

In some examples, separate charging wand 326 may facilitate positioning of coil 348 over coil 216 of IMD 210. In some examples, charging circuitry 368 and/or coil 329 may be integrated within housing 324 in other examples, as described above in relation to FIG. 1. In other examples, recharger 322 may not include charging wand 326. Memory 352 may store instructions that, when executed by processing circuitry 350, causes processing circuitry 350 and external computing device 322 to provide the functionality ascribed to external computing device 322 throughout this disclosure, and/or any equivalents thereof. Coil 348 and coil 329 may also be referred to as an antenna.

External computing device 322 may also include one or more temperature sensors, illustrated as temperature sensor 359, similar to temperature sensor 39 of FIG. 2. As shown in FIG. 3, temperature sensor 359 may be disposed within charging head 326. In other examples, one or more temperature sensors of temperature sensor 359 may be disposed within housing 324. For example, charging head 326 may include one or more temperature sensors positioned and configured to sense the temperature of coil 348 and/or a surface of the housing of charging head 326. In some examples, external computing device 322 may not include temperature sensor 359.

In general, external computing device 322 comprises any suitable arrangement of hardware, alone or in combination with software and/or firmware, to perform the techniques ascribed to external computing device 322, and processing circuitry 350, user interface 354, telemetry circuitry 356, and charging circuitry 358 of external computing device 322, and/or any equivalents thereof. In various examples, external computing device 322 may include one or more processors, such as one or more microprocessors, DSPs, ASICs, FPGAs, or any other equivalent integrated or discrete logic circuitry, as well as any combinations of such components. External computing device 322 also, in various examples, may include a memory 352, such as RAM, ROM, PROM, EPROM, EEPROM, flash memory, a hard disk, a CD-ROM, comprising executable instructions for causing the one or more processors to perform the actions attributed to them. Moreover, although processing circuitry 350, telemetry circuitry 356, charging circuitry 358, and temperature sensor 359 are described as separate modules, in some examples, processing circuitry 350, telemetry circuitry 356, charging circuitry 358, and/or temperature sensor 359 are functionally integrated. In some examples, processing circuitry 350, telemetry circuitry 356, charging circuitry 358, and/or temperature sensor 359 correspond to individual hardware units, such as ASICs, DSPs, FPGAs, or other hardware units.

Memory 352 may store instructions that, when executed by processing circuitry 350, cause processing circuitry 350 and external computing device 322 to provide the functionality ascribed to external computing device 322 throughout this disclosure, and/or any equivalents thereof. For example, memory 352 may include instructions that cause processing circuitry 350 to control the power level used to charge IMD 210 in response to the determined temperatures for the housing/external surface(s) of IMD 210, as communicated from IMD 210, or instructions for any other functionality. Memory 352 may include a record of selected power levels, sensed temperatures, determined temperatures, or any other data related to charging rechargeable power source 18, described above in relation to FIG. 2. Processing circuitry 350 may, when requested, transmit any stored data in memory 352 to another computing device for review or further processing, such as to network computing device 312.

Network computing device 312 act as a server, such as a cloud based server, or a household server. In some examples network computing device 312 may be a tablet computer, laptop computer, desktop computer, mobile phone and so on. Network computing device 312 may include a user interface which may display outputs and accept inputs, such as the state of a patient's symptoms, as described above in relation to FIGS. 1 and 2. In this manner, a user interface of network computing device 312 may be described as being operatively coupled to processing circuitry 350 as well as to processing circuitry 230 depicted in FIG. 2.

User interface 354 may also receive user input. The input may be, for example, in the form of pressing a button on a keypad or selecting an icon from a touch screen. In some examples, the input may change programmed settings, start or stop therapy, request starting or stopping a recharge session, a desired level of charging, or one or more statistics related to charging rechargeable power source 18 (e.g., the cumulative thermal dose). In this manner, user interface 354 may allow the user to view information related to the operation of IMD 210.

As described above in relation to FIGS. 1 and 2, processing circuitry 350 may cause the user interface to present a stimulation pattern construct collection to a user. The construct collection may include a variety of elements for electrical stimulation therapy. Some examples of elements may include defined waveforms, such as a positive pulse, a negative pulse, a biphasic pulse, a square waveform, triangular waveform and so on. Other examples of elements for electrical stimulation therapy may include continuous pulse trains, bursts of pulses, ramping patterns of pulses, e.g., gradually increasing and/or decreasing the pulse magnitude, pulse width, duty cycle and so on. Other elements may include linking changes in one parameter to changes in another parameter, including a randomized change between two or more patterns, a schedule of patterns, with each pattern running for a specified duration, alarms that may interrupt a scheduled pattern based on a timer or another triggering event, such as a sensed signal, and any combination of therapy elements.

In some examples, user interface 354 may present all available stimulation patterns that have been validated and approved for use. In other examples, one or more stimulation patterns, and/or therapy regimens comprising multiple stimulation patterns, may be abstracted into categories or similar groupings to simplify the user's selections. For example, the user may select a condition, such as Parkinson's disease, incontinence or similar condition. Processing circuitry 350 may cause user interface 354 to display a subset of stimulation patterns from the library of stimulation constructs particular to the selected condition. For example, user interface 354 may present the user with a subset of stimulation constructs, patterns and or therapy regimens associated with tibial nerve control of incontinence, based on the user's selection.

User interface 354 may receive an input from a user to define a stimulation pattern. User interface 354 may present selections and controls to the user and receive commands to define various parameters for each stimulation pattern, which in some examples may be customized patterns made up of approved stimulation constructs, e.g., biphasic waveforms, amplitude and/or pulse width ramping patterns, and so on. Processing circuitry 350 may execute programming instructions, e.g., stored at memory 352 and compile the defined stimulation pattern selected by the user into the instructions configured to be executed by the processing circuitry of a medical device, e.g., IMD 210. Processing circuitry 350 may output the instructions to the medical device via communication circuitry, e.g., telemetry circuitry 356, or in some examples, via inductive coupling using recharge circuitry 368 or 358.

Charging circuitry 358 may include one or more circuits that generate an electrical signal, and an electrical current, within primary coil 348. Charging circuitry 358 may generate an alternating current of specified amplitude and frequency in some examples. In other examples, charging circuitry 358 may generate a direct current. In any case, charging circuitry 358 may be capable of generating electrical signals, and subsequent magnetic fields, to transmit various levels of power to IMD 210. In this manner, charging circuitry 358 may be configured to charge rechargeable power source 18 of IMD 210 with the selected power level.

Power source 360 may deliver operating power to the components of external computing device 322. Power source 360 may also deliver the operating power to drive primary coil 348 during the charging process. Power source 360 may include a battery and a power generation circuit to produce the operating power. In some examples, a battery of power source 360 may be rechargeable to allow extended portable operation. In other examples, power source 360 may draw power from a wired voltage source such as a consumer or commercial power outlet.

Telemetry circuitry 356 supports wireless communication between IMD 210 and external computing device 322 under the control of processing circuitry 350. Telemetry circuitry 356 may also be configured to communicate with another computing device via wireless communication techniques, or direct communication through a wired connection. In some examples, telemetry circuitry 356 may be substantially similar to telemetry circuitry 236 of IMD 210 described herein, providing wireless communication via an RF or proximal inductive medium, e.g., using coil 348. In some examples, telemetry circuitry 356 may include an antenna 357, which may take on a variety of forms, such as an internal or external antenna. Although telemetry modules 356 and 36 may each include dedicated antennas for communications between these devices, telemetry modules 356 and 36 may instead, or additionally, be configured to utilize inductive coupling from coils 216 and 348 to transfer data.

Examples of local wireless communication techniques that may be employed to facilitate communication between external computing device 322 and IMD 210 include radio frequency and/or inductive communication according to any of a variety of standard or proprietary telemetry protocols, or according to other telemetry protocols such as the IEEE 802.11x or Bluetooth specification sets. In this manner, other external devices may be capable of communicating with external computing device 322 without needing to establish a secure wireless connection.

Figures 4A, 4B:
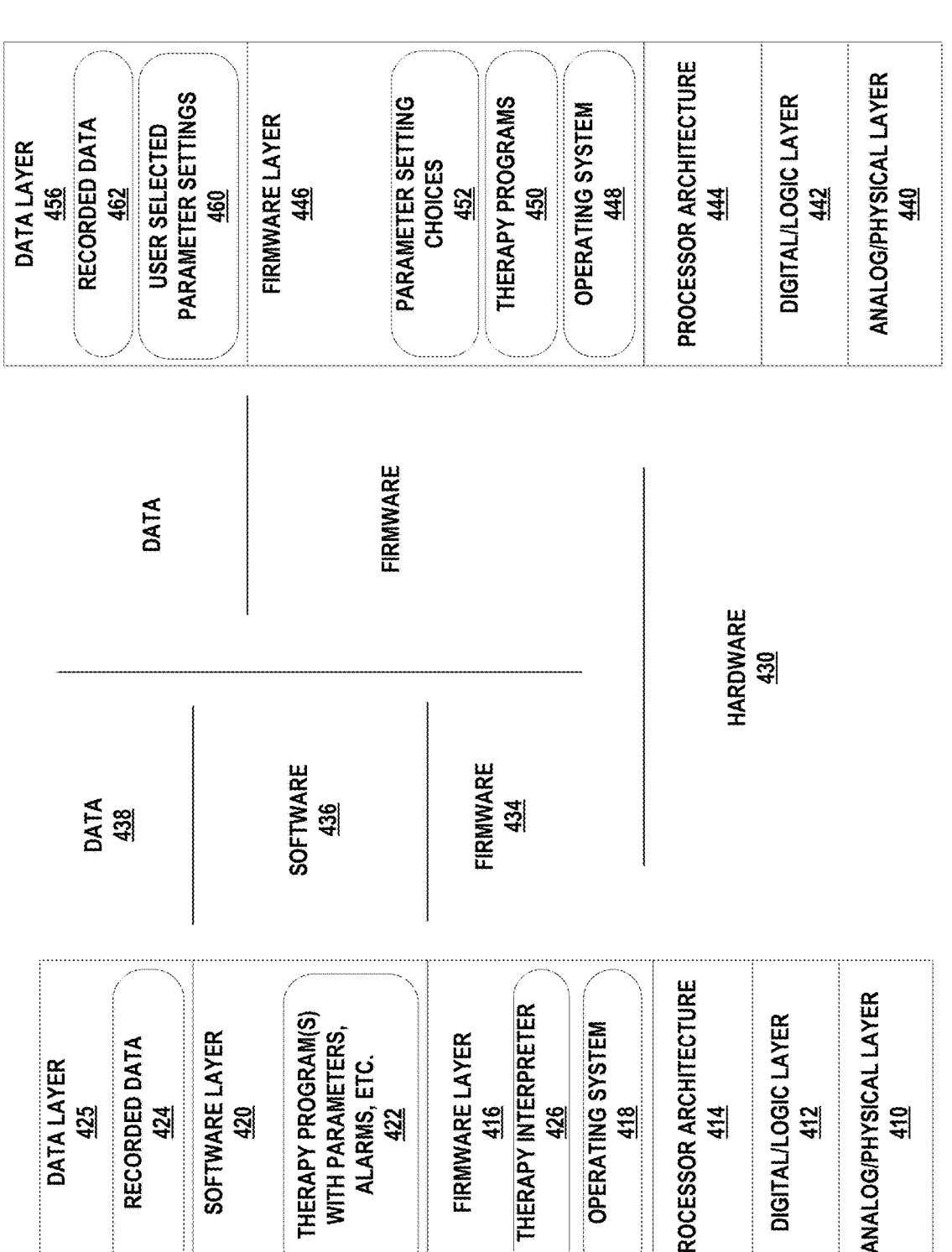
FIGS. 4A and 4B are conceptual diagrams illustrating two different examples of structures that may be implemented in an implantable medical device to deliver electrical stimulation according to one or more techniques of this disclosure.

FIGS. 4A and 4B are conceptual diagrams illustrating two different examples of structures that may be implemented in an implantable medical device to deliver electrical stimulation according to one or more techniques of this disclosure. FIG. 4A is an example implementation of IMD 110 and IMD 210 described above in relation to FIGS. 1 and 2.

FIG. 4A depicts a layer view of components of IMD 210 of FIG. 2. For example, any of processing circuitry 230, memory 232, telemetry circuitry 236 and so on may make up physical layer 410, logic layer 412, processor architecture 414 and other layers of FIG. 4A, whether the components of IMD 210 are implemented as a single integrated circuit or as multiple connected components.

Memory 232 may include firmware 434 on firmware layer 416, software 436 on software layer 420 and data 438 on data layer 425. The arrangement of FIG. 4A is one example arrangement configured to implement the techniques of this disclosure, and is just for the purpose of illustration. In other examples, other arrangements (not shown in FIG. 4A) may also implement the techniques of this disclosure. In the example of FIG. 4A, firmware layer 416 may include an operating system 418, which may include instructions on how to interact with the processor architecture 414, and perform other low level functions. Processor architecture 414 may include the boundary between software and hardware. In some examples, operating system 418 may include instructions on operating communications functions, recharging functions, timers, alarms, errors and so on. In other examples, one or more functions may be separate from operating system 418 (not shown in FIG. 4A).

Therapy interpreter 426 may be firmware configured to retrieve and interpret defined stimulation patterns stored in therapy programs 422 on software layer 420. Therapy interpreter 426 may also include instructions to be executed by processing circuitry directed to controlling the electrical stimulation circuitry in hardware 430. As described above in relation to FIGS. 1 and 2, therapy programs 422 may store a therapy regimen with a plurality of defined stimulation patterns received from the external computing device.

In some examples a caregiver may replace the therapy regimen with a different therapy regimen based on the needs of the patient. For example, the caregiver may select from the displayed collection of stimulation constructs a different stimulation pattern or patterns to create a second therapy regimen. The processing circuitry of the programmer may generate software based on the second therapy regimen and transmit the updated software to the therapy delivery device, e.g., IMD 14 described above in relation to FIGS. 1 and 2. In some examples, processing circuitry of the therapy delivery device may delete the first software defining the first therapy regimen and replace the contents of therapy programs 422 with the second received software defining the second therapy regimen. The processing circuitry, executing the same firmware in firmware layer 416 may control the therapy delivery circuitry based on the second software.

In other examples, the second software may include instructions to keep the first software and first therapy regimen stored in therapy programs 422. The processing circuitry, executing the same firmware, e.g., therapy interpreter 416 and operating system 418, may control the therapy delivery circuitry based on the instructions in the second software. For example, the second software may include instructions to delivery therapy patterns in the first software intermingled with the new therapy patterns in the second software, or based on certain triggering events.

In some examples, data layer 425 may store information, such as recorded data 424. Some examples of stored information may include temperature measurements, date and duration of a recharging session, measured bioelectrical signals and so on.

In contrast to the example of FIG. 4A, FIG. 4B does not include a software layer. The hardware 430 of the implementation in FIG. 4B may be similar to that of FIG. 4A. Also, the implementation of FIG. 4B may store recorded data 462 in data layer 456, which may include similar information, e.g., measured bioelectrical signals. Operating system 448 may include similar functions as with operating system 418, e.g., control of communication, recharging and so on. In other words, processor architecture 444, digital/logic layer 442 and analog/physical layer 440 may have a similar structure and operate in a similar manner to processor architecture 414, digital/logic layer 412 and analog/physical layer 410 of FIG. 4A. However, unlike firmware layer 416 of FIG. 4A, firmware layer 446 may include detailed instructions of therapy programs 450 and associated parameter options 452, such as an allowed range of electrical current amplitude, an allowed range of pulse widths and so on. Any parameters selected by the user, e.g., a pulse magnitude of ten microamps, a burst of four pulses, and so on, may be saved in the user selected parameter settings 460 in data layer 456. Firmware layer 446 may also include instructions to account for interactions between parameters. For example increasing a pulse repetition rate may limit the available pulse width.

As described above in relation to FIG. 2, processing circuitry executing the firmware of FIG. 4B may receive instructions from an external programmer that may include a selection from one of the available stimulation patterns in therapy programs 450, as well as one or more parameter selections from parameter options 452. However, in contrast to the implementation of FIG. 4A, to add a new stimulation pattern to therapy programs 450 would require replacing the firmware in firmware layer 446 with a new version of firmware. Adding a new electrical stimulation pattern, or combination of patterns, not already stored at therapy programs 450 would not be something a healthcare provider could do in the example of FIG. 4B. However, in the example of FIG. 4A, the definition, design, selection, assembly of stimulation patterns is removed to the external computing device, e.g., external computing device 150 of FIG. 1, rather than being locked into the firmware as in the example of FIG. 4B. A healthcare provider may replace the therapy regimen stored in software layer 420 with a different therapy regimen.

The example of FIG. 4A may provide advantages over the implementation depicted in FIG. 4B. For example, a newly tested and validated therapy pattern may be added to the external computing device, and sent to a medical electrical stimulation device configured as shown in FIG. 4A as instructions to be executed with therapy interpreter 426. However, to implement the same newly tested and validated therapy pattern may need to wait for a larger firmware update project. Making small changes to the firmware in firmware layer 446 may be cost prohibitive because of the extensive testing, reporting, submission and approval process needed for each firmware update. In contrast, the firmware in firmware layer 416 of FIG. 4A may not change. A new therapy regimen may be tested, validated and approved separately from a complete device revalidation, as needed for firmware change in the example of FIG. 4B.

Figure 5:
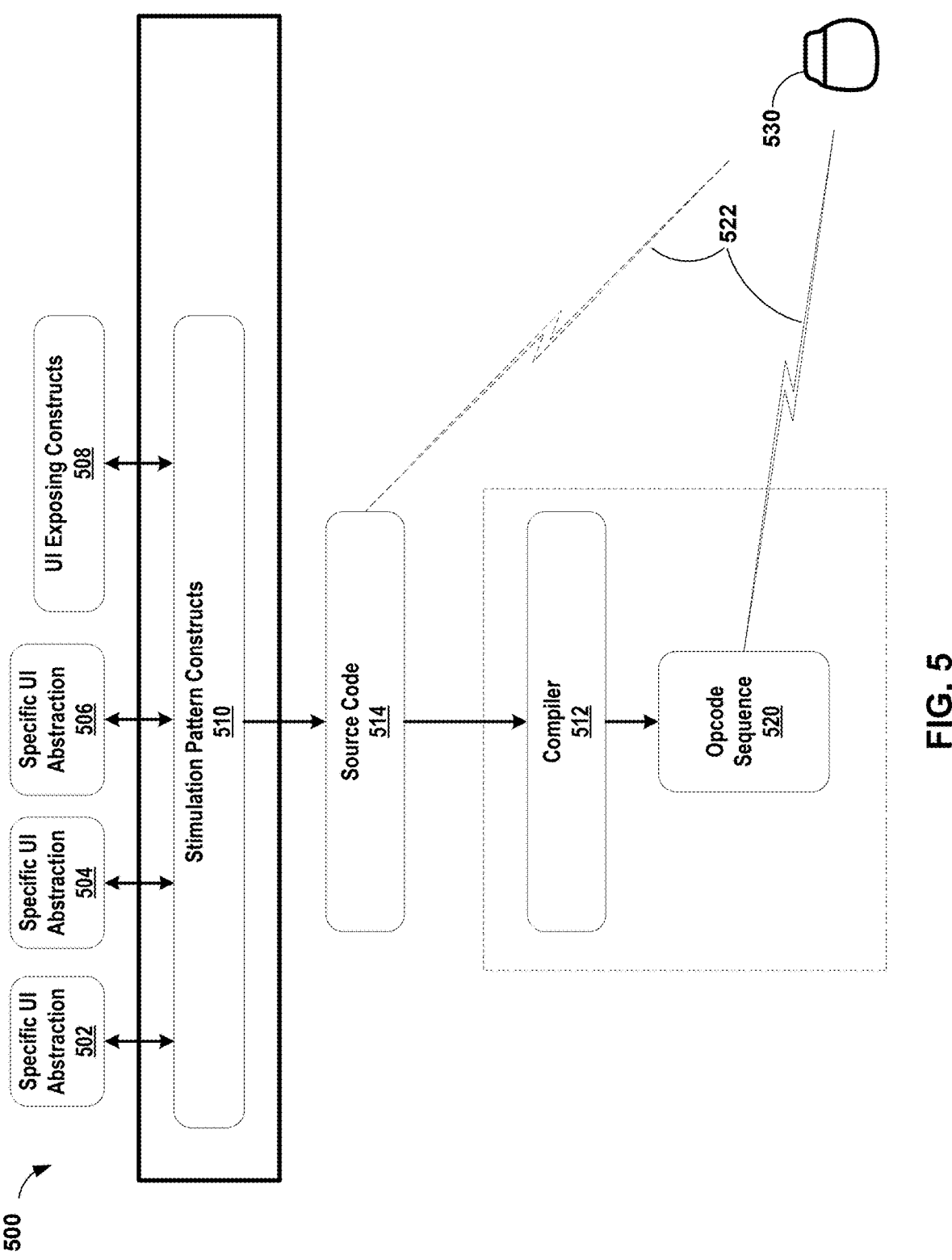
FIG. 5 is a conceptual diagram illustrating an example framework for the operation of the external computing device according to one or more techniques of this disclosure.

FIG. 5 is a conceptual diagram illustrating an example framework for the operation of the external computing device according to one or more techniques of this disclosure. The example of FIG. 5 illustrates functionality of external computing device 150 and external computing device 322 described above in relation to FIGS. 1 and 3, respectively. IMD 530 is an electrical stimulation delivery device and an example of IMD 110 and IMD 210 described above in relation to FIGS. 1 and 2.

System 500 may be an example of system 100 described above in relation to FIG. 1. In the example of FIG. 5, system 500 may include IMD 530 as well as an example arrangement of components of an external computing device, a memory storing stimulation pattern constructs 510, compiler 512, opcode sequencer 520 and processing circuitry (not shown in FIG. 5), such as processing 350 depicted in FIG. 3.

The external computing device, also called a programmer in this disclosure, may store a variety of stimulation pattern constructs 510 at a memory accessible by processing circuitry of the external computing device, e.g., via user interface UI 508. The stimulation patterns constructs may be tested, validated and approved for use for particular diseases or patient conditions. The stimulation pattern constructs may provide a common language and framework of approved stimulation pattern components, such as burst patterns, biphasic waveforms, and so on. A clinician may select, assemble, and modify waveforms, bursts, patterns etc. from the stimulation pattern construct collection via a user interface to create a therapy regimen that can be modified as needed, e.g., as the patient's disease progresses, and as new patterns become available after approval. In some examples, one or more stimulation pattern constructs 510 may be available for direct manipulation, e.g., via user interface 508. In the example of a testing environment, stimulation pattern constructs may be customized and manipulated to develop new stimulation patterns.

As described above in relation to FIG. 3, in some examples some of stimulation pattern constructs 510 may be abstracted, e.g., organized into subgroups, for easier configuration for a user, such as a health care provider. The example of FIG. 5 depicts three UI abstractions, UI abstraction 502, UI abstraction 504 and UI abstraction 506 which may include a subset of stimulation patterns and therapy regimens specific to patient needs. In some examples, UI abstraction 502 may be specific to tibial nerve stimulation, UI abstraction 504 may be specific to a patient condition such as movement disorders, pain and so on, UI abstraction 506 may be specific to cardiac stimulation devices. System 500 may include any number of specific UI abstractions that simplify selection and configuration for a user.

A compiler 512 of the external computing device may compile the stimulation patterns, which may be arranged as one or more therapy regimens. Compiler 512 may compile the selected patterns, regimen or suite of regimens into machine instructions, e.g., into opcode sequences 520. The opcode sequences 520 may be downloaded via communication channel 522 to the software portion of the memory of therapy delivery device 530, e.g., memory 232 depicted in FIG. 2 and software layer 420 depicted in FIG. 4A. The therapy delivery device, IMD 530 may "play" the instructions, e.g., opcodes 520 to output the therapy regimen. Communication channel 522 may be implemented using telemetry circuitry 236 and 356, or via the primary and secondary coils as described above in relation to FIGS. 2 and 3.

As described above in relation to FIG. 1, in some examples, compiler 512 may be located at the external computing device and compile source code 514 into opcode sequences 520. In other examples, the external computing device may download source code 514 to device 530 via communication channel 522. A compiler located as part of firmware of device 530 (not shown in FIG. 5) may receive the transmitted software in the form of source code 514 and compile the software into machine instructions.

Figures 6A, 6B, 6C:
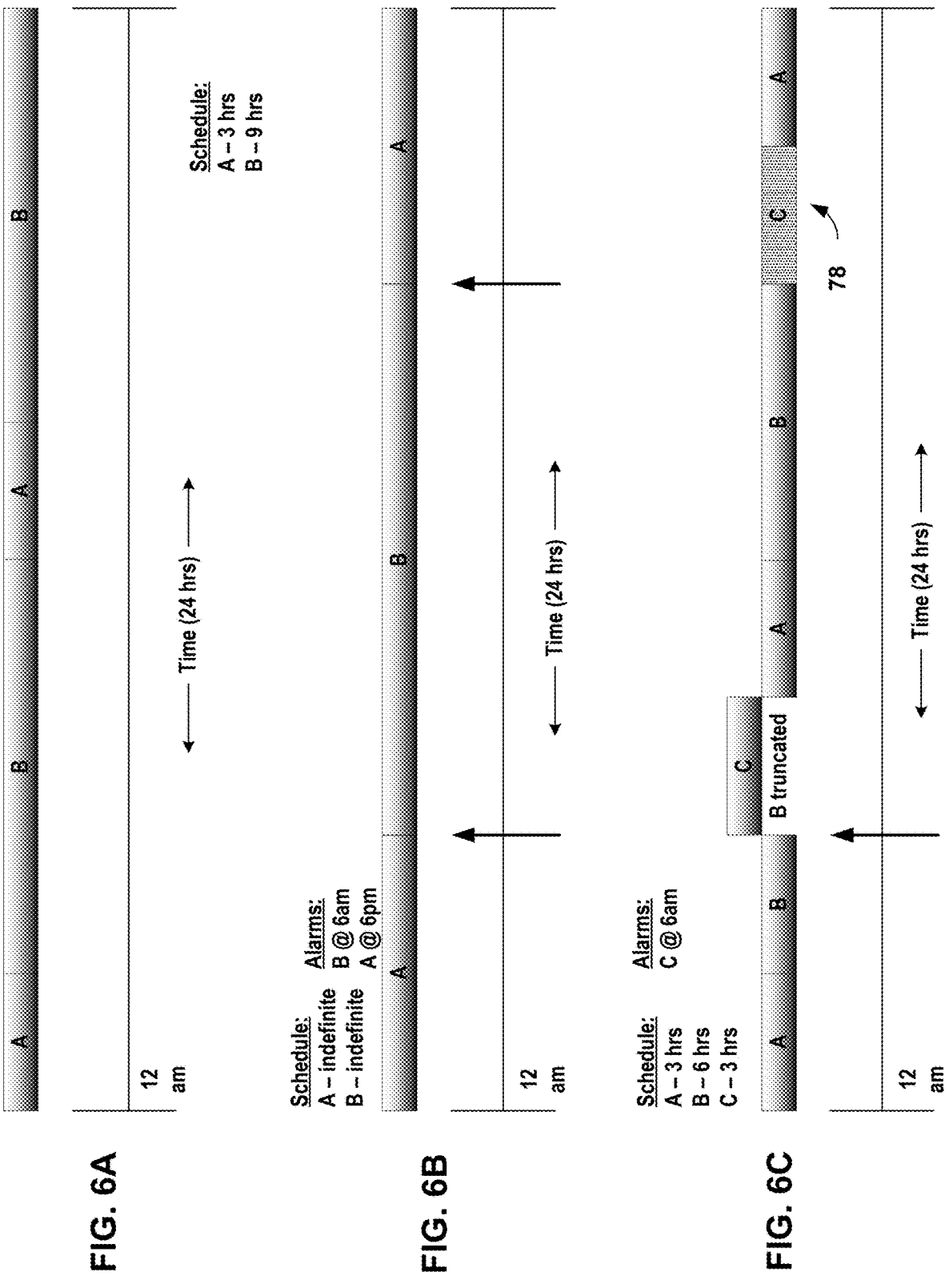
FIGS. 6A-6C are timing diagrams illustrating example therapy patterns that may be executed by a medical device according to one or more techniques of this disclosure.

FIGS. 6A-6C are timing diagrams illustrating example stimulation patterns including one or more alarms that may be executed by a medical device according to one or more techniques of this disclosure. FIG. 6A depicts a therapy regimen over a time frame of twenty four hours of a day. The regimen in the example of FIG. 6A includes a first pattern A for a duration of three hours alternating with a second pattern B for a duration of nine hours.

FIG. 6B depicts a therapy regimen with patterns A and B, each of which run for an indefinite period of time. The therapy regimen of FIG. 6B includes two alarms based on time of day. At 6 a.m. pattern B starts and at 6 p.m. pattern A starts. In other examples, the alarms may be set for any other times of day and may coincide with expected waking and sleeping cycles for the patient.

FIG. 6C depicts a therapy regimen with pattern A set for a three hour duration followed by pattern B set for a six hour duration, followed by pattern C set for a 3 hour duration. In the example of FIG. 6C, based on an alarm at 6 am, which may be triggered by the time, or some other event, the processing circuitry inserts new pattern C and truncates the duration of pattern B. Pattern C is set for a three hour duration. After the duration of pattern C expires, the processing circuitry causes the electrical stimulation circuitry to deliver therapy according to patterns A, B and C for each respective duration.

In the example of FIG. 6C, pattern C may always follow pattern B when pattern B is done. But C can and will interrupt any other pattern at 6 am, even if that pattern is not done yet, which is pattern B in the example of FIG. 6C.

Figures 7A, 7B:
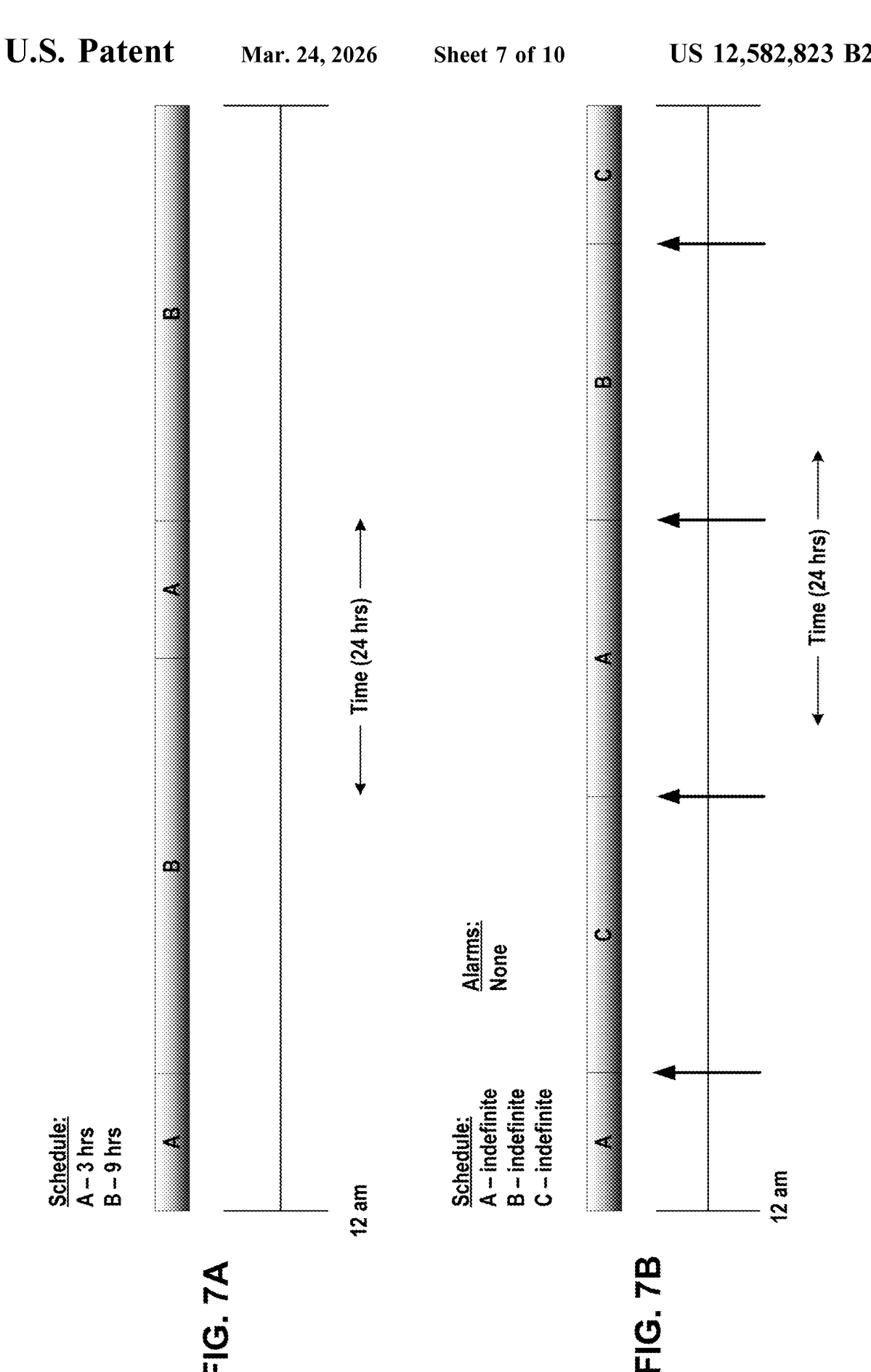
FIGS. 7A-7B are timing diagrams illustrating example therapy patterns according to one or more techniques of this disclosure.

FIGS. 7A-7B are timing diagrams illustrating example therapy regimens that may be executed by a medical device according to one or more techniques of this disclosure. FIG. 7A depicts a two pattern regimen, similar to that of FIG. 6A. Pattern A has a first duration, which in the example of FIG. 7A is three hours. The duration for pattern B in this example is nine hours, after which pattern A begins again.

FIG. 7B depicts a scenario where the therapy patterns do not have any order or duration associated with them. Instead, they reside in the device as a repository of patterns. The processing circuitry executing the firmware may invoke a selected pattern asynchronously. The arrows represent external telemetry events that instruct the device to deliver a new pattern from within the repository of patterns. Note also that in this style of pattern delivery, one pattern within the repository may be designated as the "starting" or initial pattern to be used at the onset of therapy delivery.

In some examples, this pattern definition techniques of external computing device 150, described above in FIGS. 1, 3 and 5, may permit the user to define the transition behavior and characteristics for when a stimulation pattern is initiated or a transition between patterns occurs. Examples of transition behaviors include gradual decrease of one pattern's parameters before the gradual increase of another pattern's parameters (i.e., ramping) to the target steady state value or attachment of a special initiating/priming/induction set of parameters that are used only at the onset of a pattern to optimize the transition into the pattern for patient comfort and/or nervous system dynamics.

Figures 8A, 8B:
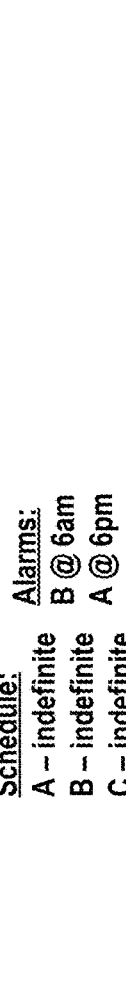
FIGS. 8A-8B are timing diagrams illustrating example therapy patterns according to one or more techniques of this disclosure.
Figure 9A:
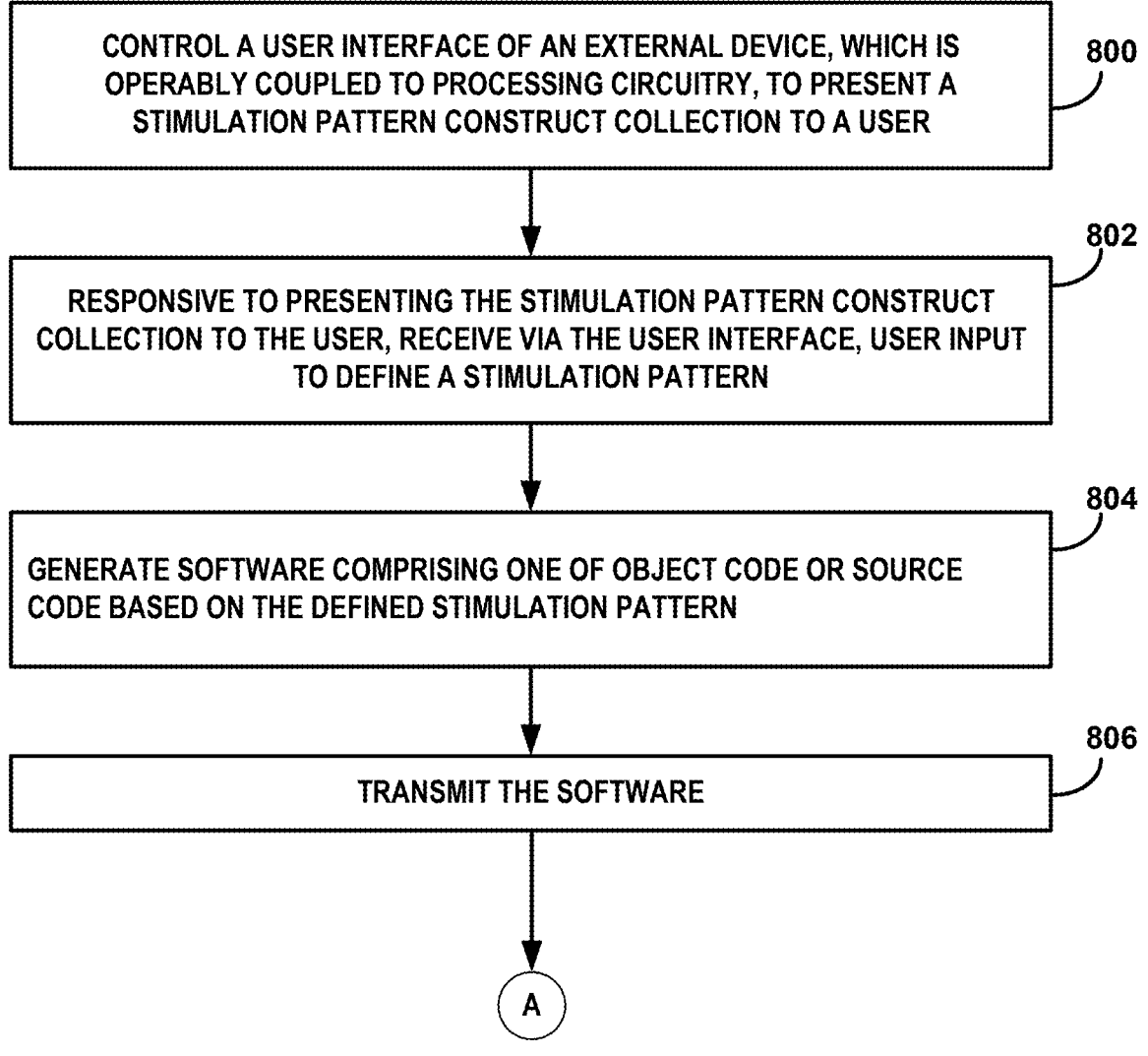
FIGS. 9A and 9B are flow charts illustrating an example operation of the system of this disclosure.

FIGS. 8A-8B are timing diagrams illustrating example therapy patterns according to one or more techniques of this disclosure. FIG. 9A depicts a therapy regimen with three defined stimulation patterns, A, B and C, each with an indefinite specified duration. Processing circuitry of the IMD would interpret the instructions stored at the software memory location when receiving the alarm at 6 am, to stop delivery of the A pattern and start delivery of the B pattern.

Pattern C starts at 720 and is not invoked via any alarms. In the example shown, the only way C can be invoked is via an asynchronous external request (e.g., telemetry). 720 represents such a scenario where the previous pattern (in this case B) is interrupted by the external request to switch to pattern C. The processing circuitry then causes pattern C to be delivered indefinitely until another alarm or request is received, in this example, the onset of A via its alarm.

Figure 9B:
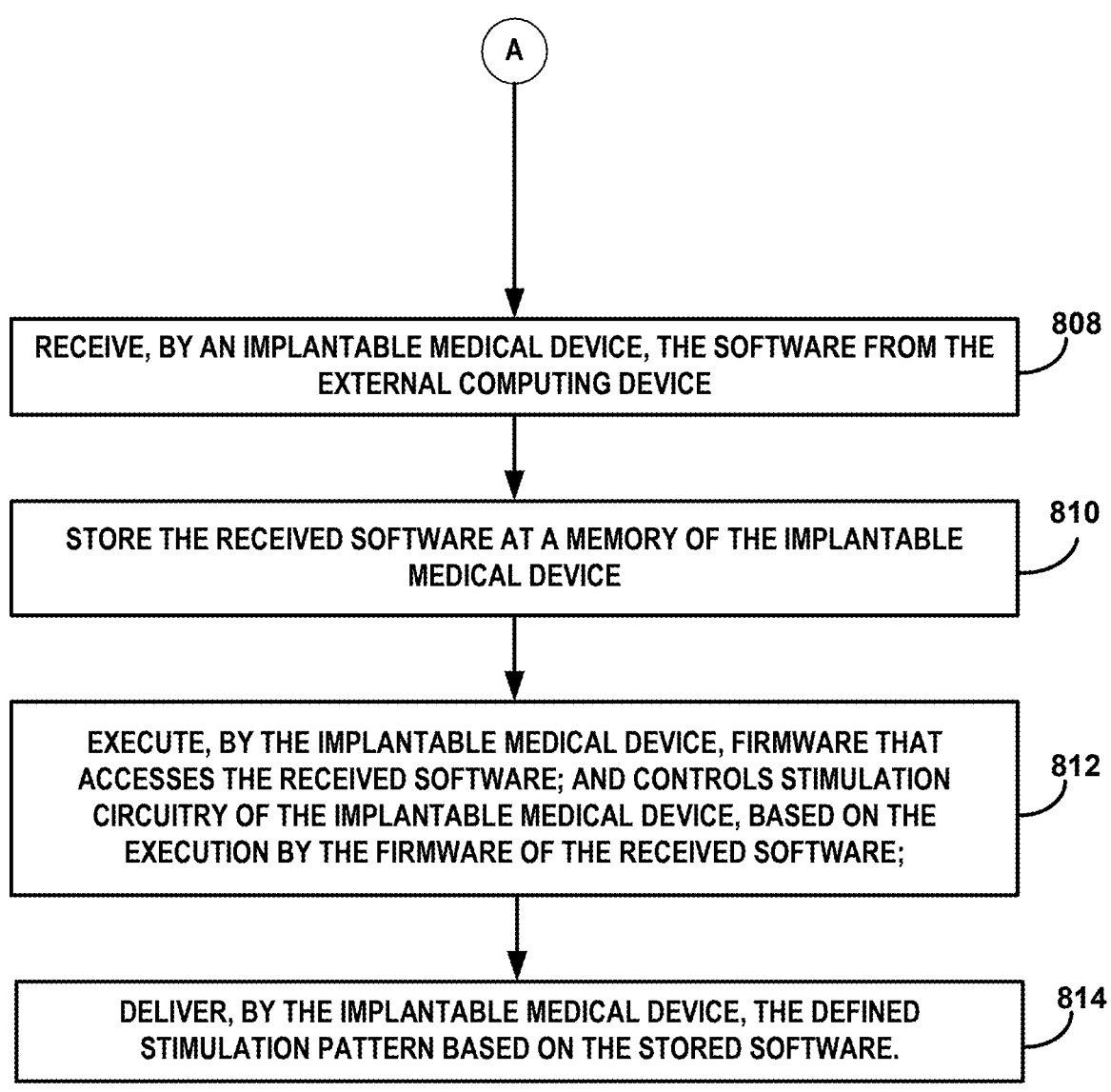

FIGS. 9A and 9B are flow charts illustrating an example operation of the system of this disclosure. Processing circuitry may refer to processing circuitry of system 100 of FIG. 1, including processing circuitry of IMD 110, external computing device 150, as well as IMD 210, external computing device 322 and network computing device 312 described above in relation to FIGS. 2 and 3.

In some examples, processing circuitry 350 of external computing device 322, may control user interface 354, operably coupled to the processing circuitry as described above, to present a stimulation pattern construct collection 510 to a user as described in FIG. 5 (800). As described above in relation to FIG. 5, stimulation pattern construct collection 510 may define a plurality of components, such as waveform shapes, patterns and so on for electrical stimulation.

Responsive to presenting the stimulation pattern construct collection to the user, e.g., with user interface 354, processing circuitry 350 may receive user input to define one or more stimulation patterns (802). The user may select the electrical stimulation patterns via user interfaces 502, 504, 506 and 508 as described above in relation to FIG. 5. Processing circuitry 350 may generate software comprising one of object code or source code based on the defined stimulation pattern (804) and transmit the software (806) via communication channel 522, as described above in relation to FIG. 5.

As shown in FIG. 9B, the implantable medical device may receive the software from the external computing device (808) and store the software at a memory of the implantable medical device, as described above in relation to FIG. 4A (810). Processing circuitry 230 of IMD 210, depicted in FIG. 2, may execute firmware 434, depicted in FIG. 4A. The firmware may access the received software from the software layer 420, which may include a therapy regimen with one or more therapy patterns as well as provisions for how to respond alarms and other triggers, as described above in relation to FIGS. 6-8B. The processing circuitry may control stimulation circuitry 234 of the implantable medical device, based on the execution by the firmware of the received software (812) to deliver the defined stimulation pattern based on the stored software (814).

The techniques of this disclosure may also be described in the following examples.

Example 1: A medical system comprising: an implantable medical device including: stimulation circuitry configured to deliver electrical stimulation to a patient via a plurality of electrodes implanted proximal to tissue of the patient; a memory configured to store software received from an external computing device, the software comprising one of object code or source code based on a defined stimulation pattern to be delivered to the patient; and processing circuitry operably coupled to the memory, the processing circuitry configured to configured to execute firmware that: causes the processing circuitry to access the received software; and controls the stimulation circuitry based on the execution of the received software to deliver stimulation according to the defined stimulation pattern.

Example 2: The medical system of example 1, wherein the software comprises a therapy regimen comprising a first defined stimulation pattern and a second defined stimulation pattern, wherein the second defined stimulation pattern is different from the first defined stimulation pattern.

Example 3: The medical system of example 2, wherein to control the stimulation circuitry, the processing circuitry is configured to execute the firmware that: controls the stimulation circuitry according to the first defined stimulation pattern for a first duration, and controls the stimulation circuitry according to the second defined stimulation pattern for a second duration.

Example 4: The medical system of example 3, wherein the therapy regimen comprises a third defined stimulation pattern, wherein the second processing circuitry is configured to: receive an indication, during the first duration or the second duration, to control the stimulation circuitry to deliver the third defined stimulation pattern, responsive to receiving the indication, the processing circuitry is configured to execute the firmware that controls the stimulation circuitry to deliver stimulation according to the third defined stimulation pattern for a third duration.

Example 5: The medical system of example 4, wherein the processing circuitry is configured to truncate the first duration or the second duration and start the third duration.

Example 6: The medical system of any of examples 4 and 5, wherein the processing circuitry is configured to start the third duration at the end of the first duration or the end of the second duration.

Example 7: The medical system of any of examples 1 through 6, wherein the tissue of the patient is nerve tissue.

Example 8: The medical system of any of examples 1 through 7, wherein the processing circuitry is first processing circuitry, and wherein the external computing device includes: a user interface comprising a display and input device; second processing circuitry operably coupled to the user interface, the second processing circuitry configured to: cause the user interface to present a stimulation pattern construct collection to a user; receive user input to define a stimulation pattern responsive to presenting the stimulation pattern construct collection to the user; generate software comprising one of object code or source code based on the defined stimulation pattern; transmit the software to the implantable medical device.

Example 9: The medical system of example 8, wherein the external computing device is configured to compile the defined stimulation pattern into the object code.

Example 10: The medical system of any of examples 8 and 9, wherein the received software is a first software, wherein the first processing circuitry is configured to receive a second software based on a second stimulation pattern different from the first software; wherein the first processing circuitry is configured to execute the firmware to access the second software and control the stimulation circuitry based on execution of the second software.

Example 11: The medical system of example 10, wherein the first processing circuitry is configured to delete the first software from the memory.

Example 12: The medical system of any of examples 10 and 11, wherein the first processing circuitry is configured to execute the firmware to control the stimulation circuitry based on both the first software and the second software.

Example 13: A method comprising: receiving, by an implantable medical device, software from an external computing device; storing, by processing circuitry of the implantable medical device, the software at a memory of the implantable medical device; executing, by the processing circuitry, firmware that: accesses the received software; and controls stimulation circuitry of the implantable medical device, based on the execution by the firmware of the received software; delivering, by the implantable medical device, the defined stimulation pattern based on the stored software.

Example 14: The method of example 13, wherein the software comprises a therapy regimen comprising a first defined stimulation pattern and a second defined stimulation pattern, wherein the second defined stimulation pattern is different from the first defined stimulation pattern.

Example 15: The method of example 14, further includes controlling the stimulation circuitry according to the first defined stimulation pattern for a first duration, and controlling the stimulation circuitry according to the second defined stimulation pattern for a second duration.

Example 16: The method of any of examples 14 and 15, wherein the therapy regimen comprises a third defined stimulation pattern, the method further includes receiving, by the implantable medical device, an indication during the first duration or the second duration to control the stimulation circuitry to deliver the third defined stimulation pattern, responsive to receiving the indication, executing, by the processing circuitry the firmware that controls the stimulation circuitry to deliver stimulation according to the third defined stimulation pattern for a third duration.

Example 17: The method of example 16, wherein delivering the third defined stimulation pattern comprises truncating the first duration or the second duration and starting the third defined stimulation pattern for the third duration.

Example 18: The method of any of examples 16 and 17, wherein delivering the third defined stimulation pattern comprises starting the third duration at the end of the first duration or the end of the second duration.

Example 19: The method of any of examples 13 through 18, wherein the tissue of the patient is nerve tissue.

Example 20: The method of any of examples 13 through 19, wherein the received software is a first software, the method further includes receiving, by the implantable medical device a second software based on a second stimulation pattern different from the first software; executing the firmware to access the second software and control the stimulation circuitry based on execution of the second software.

Example 21: The method of example 20, further comprising deleting, by the firmware, the first software from the memory.

Example 22: The method of any of examples 20 and 21, further comprising controlling, by the firmware, the stimulation circuitry based on both the first software and the second software.

Example 23: The method of any of examples 13 through 22, further includes controlling, by second processing circuitry of an external computing device, a user interface operably coupled to the processing circuitry, to present a stimulation pattern construct collection to a user, wherein the stimulation pattern construct collection defines a plurality of elements for electrical stimulation; responsive to presenting the stimulation pattern construct collection to the user, receiving by the second processing circuitry and via the user interface, user input to define a stimulation pattern; generating, by the second processing circuitry, software comprising one of object code or source code based on the defined stimulation pattern; transmitting, by the second processing circuitry, the software to the implantable medical device.

In one or more examples, the functions described above may be implemented in hardware, software, firmware, or any combination thereof. For example, the various components of FIGS. 2 and 3, such as processing circuitry 230, telemetry circuitry 236, therapy and sensing circuitry 234 102, processing circuitry 350, user interface 354 and so on may be implemented in hardware, software, firmware, or any combination thereof. If implemented in software, the functions may be stored on or transmitted over, as one or more instructions or code, a computer-readable medium and executed by a hardware-based processing unit. Computer-readable media may include computer-readable storage media, which corresponds to a tangible medium such as data storage media, or communication media including any medium that facilitates transfer of a computer program from one place to another, e.g., according to a communication protocol. In this manner, computer-readable media generally may correspond to (1) tangible computer-readable storage media which is non-transitory or (2) a communication medium such as a signal or carrier wave. Data storage media may be any available media that can be accessed by one or more computers or one or more processors to retrieve instructions, code and/or data structures for implementation of the techniques described in this disclosure. A computer program product may include a computer-readable medium, such as memory 352 and memory 232.

The term "non-transitory" may indicate that the storage medium is not embodied in a carrier wave or a propagated signal. In certain examples, a non-transitory storage medium may store data that can, over time, change (e.g., in RAM or cache). By way of example, and not limitation, such computer-readable storage media, may include random access memory (RAM), read only memory (ROM), programmable read only memory (PROM), erasable programmable read only memory (EPROM), electronically erasable programmable read only memory (EEPROM), flash memory, a hard disk, a compact disc ROM (CD-ROM), a floppy disk, a cassette, magnetic media, optical media, or other computer readable media. In some examples, an article of manufacture may include one or more computer-readable storage media.

Also, any connection is properly termed a computer-readable medium. For example, if instructions are transmitted from a website, server, or other remote source using a coaxial cable, fiber optic cable, twisted pair, digital subscriber line (DSL), or wireless technologies such as infrared, radio, and microwave, then the coaxial cable, fiber optic cable, twisted pair, DSL, or wireless technologies such as infrared, radio, and microwave are included in the definition of medium. It should be understood, however, that computer-readable storage media and data storage media do not include connections, carrier waves, signals, or other transient media, but are instead directed to non-transient, tangible storage media. Combinations of the above should also be included within the scope of computer-readable media.

Instructions may be executed by one or more processors, such as one or more DSPs, general purpose microprocessors, ASICs, FPGAs, or other equivalent integrated or discrete logic circuitry. Accordingly, the term "processor," as used herein, may refer to any of the foregoing structure or any other structure suitable for implementation of the techniques described herein. Also, the techniques could be fully implemented in one or more circuits or logic elements.

The techniques of this disclosure may be implemented in a wide variety of devices or apparatuses, including, an integrated circuit (IC) or a set of ICs (e.g., a chip set). Various components, modules, or units are described in this disclosure to emphasize functional aspects of devices configured to perform the disclosed techniques, but do not necessarily require realization by different hardware units. Rather, as described above, various units may be combined in a hardware unit or provided by a collection of interoperative hardware units, including one or more processors as described above, in conjunction with suitable software and/or firmware.

Various examples of the disclosure have been described. These and other examples are within the scope of the following claims.

What is claimed is:

1. A medical system comprising:
an implantable medical device including:
    stimulation circuitry configured to deliver electrical stimulation to a patient via a plurality of electrodes implanted proximal to tissue of the patient;
    a memory configured to store software received from an external computing device, the software comprising one of object code or source code based on a defined stimulation pattern to be delivered to the patient; and
    processing circuitry operably coupled to the memory, the processing circuitry configured to execute firmware that:
    causes the processing circuitry to access the received software; and
    controls the stimulation circuitry based on the execution of the received software to deliver stimulation according to the defined stimulation pattern.

2. The medical system of claim 1, wherein the software comprises a therapy regimen comprising a first defined stimulation pattern and a second defined stimulation pattern, wherein the second defined stimulation pattern is different from the first defined stimulation pattern.

3. The medical system of claim 2, wherein to control the stimulation circuitry, the processing circuitry is configured to execute the firmware that:
    controls the stimulation circuitry according to the first defined stimulation pattern for a first duration, and
    controls the stimulation circuitry according to the second defined stimulation pattern for a second duration.

4. The medical system of claim 3, wherein the therapy regimen comprises a third defined stimulation pattern, wherein the processing circuitry is configured to:
    receive an indication, during the first duration or the second duration, to control the stimulation circuitry to deliver the third defined stimulation pattern,
    responsive to receiving the indication, the processing circuitry is configured to execute the firmware that controls the stimulation circuitry to deliver stimulation according to the third defined stimulation pattern for a third duration.

5. The medical system of claim 4, wherein the processing circuitry is configured to truncate the first duration or the second duration and start the third duration.

6. The medical system of claim 4, wherein the processing circuitry is configured to start the third duration at an end of the first duration or the end of the second duration.

7. The medical system of claim 1, wherein the tissue of the patient is nerve tissue.

8. The medical system of claim 1, wherein the processing circuitry is first processing circuitry, and wherein the external computing device includes:
    a user interface comprising a display and input device;
    second processing circuitry operably coupled to the user interface, the second processing circuitry configured to:
    cause the user interface to present a stimulation pattern construct collection to a user;
    receive user input to define a stimulation pattern responsive to presenting the stimulation pattern construct collection to the user;
    generate software comprising one of object code or source code based on the defined stimulation pattern; and
    transmit the software to the implantable medical device.

9. The medical system of claim 8, wherein the external computing device is configured to compile the defined stimulation pattern into the object code.

10. The medical system of claim 8, wherein the received software is a first software, wherein the first processing circuitry is configured to receive a second software based on a second stimulation pattern different from the first software; wherein the first processing circuitry is configured to execute the firmware to access the second software and control the stimulation circuitry based on execution of the second software.

11. The medical system of claim 10, wherein the first processing circuitry is configured to delete the first software from the memory.

12. The medical system of claim 10, wherein the first processing circuitry is configured to execute the firmware to control the stimulation circuitry based on both the first software and the second software.

13. A method comprising:

receiving, by an implantable medical device, software from an external computing device, the software comprising one of object code or source code based on a defined stimulation pattern to be delivered to tissue of a patient;

storing, by processing circuitry of the implantable medical device, the software at a memory of the implantable medical device;

executing, by the processing circuitry, firmware that:

accesses the received software; and controls stimulation circuitry of the implantable medical device, based on the execution by the firmware of the received software; and delivering, by the implantable medical device, the defined stimulation pattern based on the stored software.

14. The method of claim 13, wherein the defined stimulation pattern software comprises a therapy regimen comprising a first defined stimulation pattern and a second defined stimulation pattern, wherein the second defined stimulation pattern is different from the first defined stimulation pattern.

15. The method of claim 14, further comprising:

controlling the stimulation circuitry according to the first defined stimulation pattern for a first duration, and controlling the stimulation circuitry according to the second defined stimulation pattern for a second duration.

16. The method of claim 15, wherein the therapy regimen comprises a third defined stimulation pattern, the method further comprising:

receiving, by the implantable medical device, an indication during the first duration or the second duration to control the stimulation circuitry to deliver the third defined stimulation pattern, responsive to receiving the indication, executing, by the processing circuitry the firmware that controls the stimulation circuitry to deliver stimulation according to the third defined stimulation pattern for a third duration.

17. The method of claim 16, wherein delivering the third defined stimulation pattern comprises truncating the first duration or the second duration and starting the third defined stimulation pattern for the third duration.

18. The method of claim 16, wherein delivering the third defined stimulation pattern comprises starting the third duration at the end of the first duration or the end of the second duration.

19. The method of claim 13, wherein the tissue of the patient is nerve tissue.

20. The method of claim 13, wherein the received software is a first software, the method further comprising:

receiving, by the implantable medical device a second software based on a second stimulation pattern different from the first software; and executing the firmware to access the second software and control the stimulation circuitry based on execution of the second software.

21. The method of claim 20, further comprising deleting, by the firmware, the first software from the memory.

22. The method of claim 20, further comprising controlling, by the firmware, the stimulation circuitry based on both the first software and the second software.

23. The method of claim 13, further comprising:

controlling, by second processing circuitry of an external computing device, a user interface operably coupled to the processing circuitry, to present a stimulation pattern construct collection to a user, wherein the stimulation pattern construct collection defines a plurality of elements for electrical stimulation;

responsive to presenting the stimulation pattern construct collection to the user, receiving by the second processing circuitry and via the user interface, user input to define a stimulation pattern;

generating, by the second processing circuitry, the software comprising one of object code or source code based on the defined stimulation pattern; and transmitting, by the second processing circuitry, the software to the implantable medical device.

* * * * *